(12) United States Patent
Zhang

(10) Patent No.: US 10,961,523 B2
(45) Date of Patent: *Mar. 30, 2021

(54) MULTILAYER NANO-CELL

(71) Applicant: Boke Zhang, Brighton, MA (US)

(72) Inventor: Boke Zhang, Brighton, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/996,457

(22) Filed: Aug. 18, 2020

(65) Prior Publication Data

US 2020/0392476 A1 Dec. 17, 2020

Related U.S. Application Data

(63) Continuation of application No. 16/419,508, filed on May 22, 2019.

(51) Int. Cl.
*C12N 9/52* (2006.01)
*A61K 9/51* (2006.01)
*A61K 31/728* (2006.01)
*A61K 38/00* (2006.01)

(52) U.S. Cl.
CPC ............ *C12N 9/52* (2013.01); *A61K 9/5123* (2013.01); *A61K 31/728* (2013.01); *C12Y 304/24069* (2013.01); *A61K 38/00* (2013.01)

(58) Field of Classification Search
None
See application file for complete search history.

(56) References Cited

U.S. PATENT DOCUMENTS 8,318,181 B2   11/2012   Edelson et al.
9,833,403 B2 *  12/2017   Liu ..................... A61K 8/9794
2017/0327811 A1  11/2017   Ton et al.

OTHER PUBLICATIONS

Singh et al. 2017 (Nanoemulsion: Concepts, development and applications in drug delivery; Journal of Controlled Release 252:28-49). (Year: 2017).

* cited by examiner

*Primary Examiner* — Mary Maille Lyons
(74) *Attorney, Agent, or Firm* — Anova Law Group, PLLC

(57) ABSTRACT

A multilayer nano-cell includes an innermost water phase core including biomolecules in an aqueous solution; a first layer, including an oil phase layer encapsulating the innermost water phase core, thereby forming a water-in-oil structure, the oil phase layer including caprylic/capric triglyceride and macrogol-35-glycerol-rizinoleat; a second layer, including a water phase layer encapsulating the first layer, the water phase layer including hyaluronic acid, Cu-GHK tripeptide, palmitoyl-KTTKS pentapeptide, and hexapeptide argireline; a third layer, including another oil phase layer encapsulating the second layer; a fourth layer, including another water phase layer encapsulating the third layer; a fifth layer, including another oil phase layer encapsulating the fourth layer; and a sixth layer, including an outmost cream layer encapsulating the fifth layer.

9 Claims, 10 Drawing Sheets

Specification includes a Sequence Listing.

Lane 1: 1st A-50 Pool  Lane 2: 2nd A-50 load
Lane 3: 2nd A-50 pool  Lane 4: Protein Std (260, 160, 110, 80, 60, 50, 40, 30, 20, 15, 10 kD)
Lane 5: SP load  Lane 6: SP Pool (Final product containing glycerol)

Case one: T = 0 (left) and T = four weeks (right)

Case two: T = 0 (left) and T = four weeks (right)

Case three: T = 0 (left) and T = four weeks (right)

Case four: T = 0 (left) and T = four weeks (right)

Case five: T = 0 (left) and T = one week (right)

Case six: T = 0 (left) and T = one week (right)

Case seven: T = 0 (left) and T = one week (right)

Case eight: T = 0 (left) and T = two weeks (right)

Case nine: T = 0 (left) and T = two weeks (right)

SEQUENCE LISTING

```
<160> NUMBER OF SEQ ID NOS: 6

<210> SEQ ID NO 1
<211> LENGTH: 26
<212> TYPE: DNA
<213> ORGANISM: Artificial Sequence
<220> FEATURE:
<223> OTHER INFORMATION: Type A Primer Pair Forward

<400> SEQUENCE: 1
gtgatacaac cagatggtag ttatag                                26

<210> SEQ ID NO 2
<211> LENGTH: 27
<212> TYPE: DNA
<213> ORGANISM: Artificial Sequence
<220> FEATURE:
<223> OTHER INFORMATION: Type A Primer Pair Reverse

<400> SEQUENCE: 2
aaaaaacaag tcccaattat taacttt                               27

<210> SEQ ID NO 3
<211> LENGTH: 27
<212> TYPE: DNA
<213> ORGANISM: Artificial Sequence
<220> FEATURE:
<223> OTHER INFORMATION: Type B Primer Pair Forward

<400> SEQUENCE: 3
gagatgtttg tgaatattat gatccag                               27

<210> SEQ ID NO 4
<211> LENGTH: 25
<212> TYPE: DNA
<213> ORGANISM: Artificial Sequence
<220> FEATURE:
<223> OTHER INFORMATION: Type B Primer Pair Reverse

<400> SEQUENCE: 4
gttcatgcat taatatcaag gctgg                                 25

<210> SEQ ID NO 5
<211> LENGTH: 24
```

-continued

```
<212> TYPE: DNA
<213> ORGANISM: Artificial Sequence
<220> FEATURE:
<223> OTHER INFORMATION: Type E Primer Pair Forward

<400> SEQUENCE: 5
ccaggcggtt gtcaagaatt ttat                                          24

<210> SEQ ID NO 6
<211> LENGTH: 24
<212> TYPE: DNA
<213> ORGANISM: Artificial Sequence
<220> FEATURE:
<223> OTHER INFORMATION: Type E Primer Pair Reverse

<400> SEQUENCE: 6
tcaaataaat caggctctgc tccc                                          24
```

MULTILAYER NANO-CELL

CROSS-REFERENCES TO RELATED APPLICATIONS

This application is a continuation of U.S. patent application Ser. No. 16/419,508, filed on May 22, 2019, the entirety of which is incorporated herein by reference.

REFERENCE TO AN ELECTRONIC SEQUENCE LISTING

The contents of the electronic sequence listing (231sequencelisting.txt; Size: 2 kilobytes; and Date of Creation: Aug. 1, 2019) is herein incorporated by reference in its entirety.

FIELD

The present disclosure generally relates to the field of protein preparation and delivery and, more particularly, relates to multilayer nano-cells.

BACKGROUND

Botulinum toxin is a neurotoxin produced by bacterium *Clostridium botulinum*, an anaerobic, gram-positive, spore-forming rod commonly found in plants, soil, water and intestinal tracts of animals. *Clostridium botulinum* elaborates seven antigenically distinguishable exotoxins (A, B, C, D, E, F and G). All serotypes interfere with neural transmission by blocking the release of acetylcholine which is the principal neurotransmitter at the neuromuscular junction, causing muscle paralysis. Botulinum neurotoxin now plays a significant role in variety of therapeutic applications, including strabismus, focal dystonia, hemifacial spasm, various spastic movement disorders, headaches, hypersalivation and hyperhidrosis, where the application list is still rapidly expanding. Botulinum neurotoxin is also commonly used in cosmetological applications, including correction of lines, creases and wrinkling all over face, chin, neck, and chest and other dermatological applications such as hyperhidrosis. In 2002, US Food and Drug Administration (FDA) approved the use of Botox® (botulinum neurotoxin A) for cosmetic purposes of temporarily reducing glabella forehead frown lines.

Botulinum neurotoxin (also called as botulinum holotoxin, or holo BoNT-A) is produced as relatively less active, the light chain and heavy chain are linked by the disulfide bridge to form the core small molecule toxin (SM Toxin or holotoxin) with molecular weight of about 150 kDa and being more active. FIG. 1 illustrates a schematic structure of botulinum neurotoxin. As illustrated in FIG. 1, the botulinum neurotoxin polypeptide chain includes a heavy (H) chain and a light (L) chain of roughly 100 kDa and 50 kDa, respectively, linked by a disulfide bridge. Botulinum neurotoxin A has a specific enzymatic activity for intraneuronal proteolytic attacking of soluble N-ethylmaleimide-sensitive factor attachment protein receptors (SNAREs), where the enzymatic activity is conferred through the L-chain. The H-chain is required for receptor binding and translocation into the cytosol. Holo BoNT-A associates with other proteins, including non-hemagglutinating proteins and hemagglutinins, to form botulinum toxin complex (also called as BoNT-A) which has greater molecular weight (e.g., 960 kDa). Unlike the 150 kDa holo BoNT-A (having toxicity as well as therapeutic effects), the associated proteins present in the botulinum toxin complex are non-toxic and therefore, not required for pharmacologic effects.

Botulinum neurotoxin has been used for a human treatment using fermentation medium containing animal-derived ingredients. However, the use of animal-derived products may cause potential contamination (e.g., virus from animal-derived products) into the prepared botulinum toxin for clinical use, which may increase the risk during therapeutic applications.

Furthermore, due to the relatively large molecular weights of both BoNT-A (960 KDa) and holo BoNT-A (150 KDa), the most common way of administration is needle injection in clinical settings. However, needle injection is inconvenient, painful and unsafe to use, with relatively low patient compliance. Hence, it is needed to develop alternative methods to realize a convenient, safe and painless delivery of botulinum neurotoxin, particularly in therapeutic, dermatological and cosmeceutical fields. For example, it is desired to develop a non-invasive delivery method for large molecular weight proteins including botulinum neurotoxin in topical applications, e.g., transdermal delivery applied by hands, rather than needle injection or other invasive delivery processes with use of an equipment.

Human skin includes a variety of layers of tissues and cells in 3-dimensional settings, such as at least stratum corneum (SC), epidermis (ED) and dermis with from 20 μm to a few hundred μm (e.g., approximately 250 μm in some facial areas) of thickness. Human skin can be generally viewed as 3-dimensional delicate multi-layered (oil-water)$_n$ system with defined network structures from outer skin cells to inner skin cells. Therefore, it is a challenge to deliver a biomolecule especially with large molecular weight, to cross a delicate and thick barrier from outer skin cells to inner skin cells.

The disclosed method for preparing botulinum neurotoxin A and its transdermal delivery in nano-encapsulations are directed to solve one or more problems set forth above and other problems in the art.

SUMMARY

One aspect of the present disclosure provides a multilayer nano-cell, including: an innermost water phase core including biomolecules in an aqueous solution, the biomolecules including hyaluronic acid, and the aqueous solution including Cu-GHK tripeptide, palmitoyl-KTTKS pentapeptide, and hexapeptide argireline; a first layer, including an oil phase layer encapsulating the innermost water phase core, thereby forming a water-in-oil structure, the oil phase layer including caprylic/capric triglyceride and macrogol-35-glycerol-rizinoleat; a second layer, including a water phase layer encapsulating the first layer, the water phase layer including hyaluronic acid, Cu-GHK tripeptide, palmitoyl-KTTKS pentapeptide, and hexapeptide argireline; a third layer, including another oil phase layer encapsulating the second layer; a fourth layer, including another water phase layer encapsulating the third layer; a fifth layer, including another oil phase layer encapsulating the fourth layer; and a sixth layer, including an outmost cream layer encapsulating the fifth layer.

One aspect of the present disclosure provides a method for preparing botulinum neurotoxin with biological activity. In the method, bacteria *Clostridium botulinum* is fermented in a fermentation media. The fermentation media is free of animal-derived ingredients. The fermentation media including the bacteria *Clostridium botulinum* contacts with an anion exchange media slurry. A supernatant including the botulinum neurotoxin is obtained by centrifugation. The supernatant is dialyzed and a dialyzed solution including the botulinum neurotoxin is collected. The dialyzed solution including the botulinum neurotoxin contacts with an anion exchange chromatography column. The dialyzing and the contacting with the anion exchange chromatography column are repeatedly performed. An elute including the botulinum neurotoxin is obtained. The elute obtained from the anion exchange chromatography column contacts with a cation exchange chromatography column. An elute including the botulinum neurotoxin obtained from the cation exchange chromatography column is obtained.

Another aspect of the present disclosure provides a nanoparticle. The nanoparticle includes an innermost water phase core including biomolecules encapsulated by an oil phase layer, thereby forming a water-in-oil structure. The biomolecules include botulinum neurotoxin and/or hyaluronic acid. The nanoparticle further includes a plurality of water phase layers; a plurality of oil phase layers; and an outmost cream layer. Each of the plurality of water phase layers and each of the plurality of oil phase layers alternatively encapsulate the water-in-oil structure.

Other aspects of the present disclosure can be understood by those skilled in the art in light of the description, the claims, and the drawings of the present disclosure.

BRIEF DESCRIPTION OF THE DRAWINGS

To describe the technical solutions in the embodiments of the present disclosure more clearly, the following briefly introduces the accompanying drawings used for describing the embodiments. Apparently, the accompanying drawings in the following description show merely some embodiments of the present disclosure, and a person skilled in the art may still derive other drawings from these accompanying drawings without creative efforts.

DESCRIPTION OF EMBODIMENTS

Although the principles and implementations of the present disclosure are described by using specific embodiments in the specification, the foregoing descriptions of the embodiments are only intended to help understand the method and core idea of the method of the present disclosure. Meanwhile, a person of ordinary skill in the art may make modifications to the specific implementations and application range according to the idea of the present disclosure. In conclusion, the content of the specification should not be construed as a limitation to the present disclosure.

Figure 1:
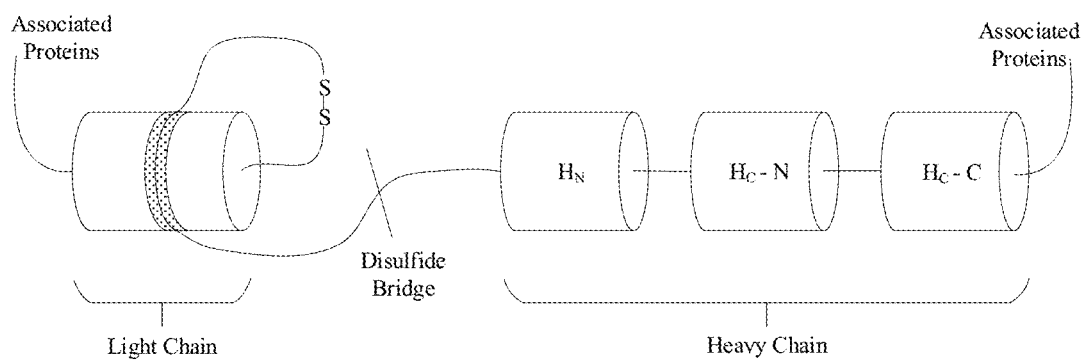
FIG. 1 illustrates schematic structure of botulinum neurotoxin.
Figure 2:
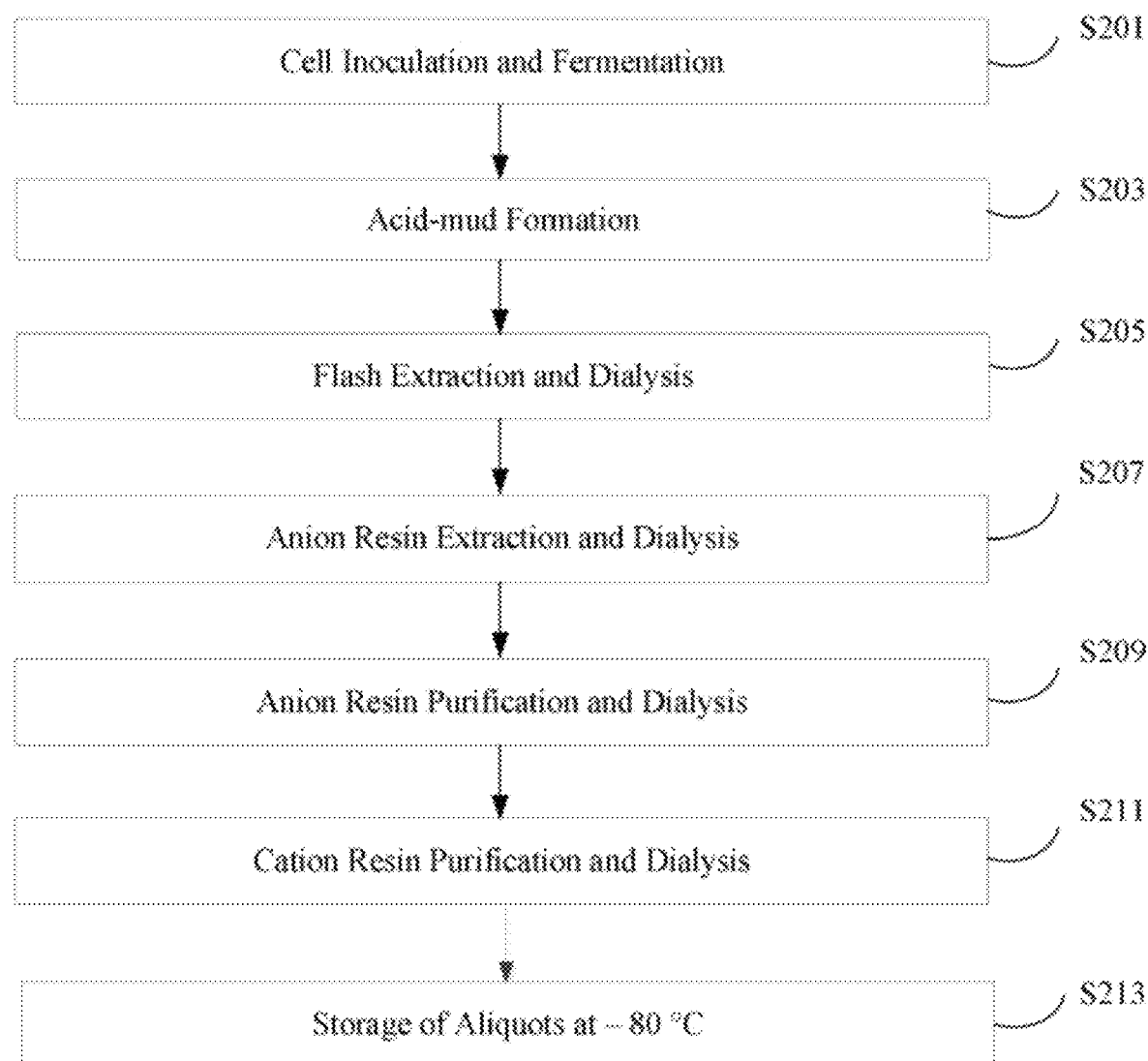
FIG. 2 illustrates a flow chart of an exemplary method for preparing botulinum neurotoxin A with small molecular weight according to various embodiments of the present disclosure.

The present disclosure provides a method for preparing botulinum neurotoxin A with small molecular weight according to various embodiments of the present disclosure. Botulinum neurotoxin A may be produced by fermentation of *Clostridium botulinum*, type A, strain Hall, and further extracted and purified from the fermentation medium. FIG. 2 illustrates a flow chart of an exemplary method for preparing botulinum neurotoxin A with small molecular weight according to various embodiments of the present disclosure.

In FIG. 2, the exemplary method may include cell inoculation and fermentation during which bacterium *Clostridium botulinum* may be cultured in a controllable manner and produce botulinum neurotoxin A (e.g., in S201 of FIG. 2). The method may further include acid-mud formation to acidify the fermentation medium at harvest in order to initiate the extraction of botulinum neurotoxin A as target protein (e.g., in S203 of FIG. 2). After the fermentation medium is acidified to form precipitate, the exemplary method may further include flash extraction and dialysis to remove nucleic acid impurities and other protein impurities (e.g., in S205 of FIG. 2). To further remove remaining nucleic acid impurities and other associated non-toxic proteins and obtain high purity of botulinum neurotoxin A with small molecular weight, the exemplary method may further include sequential purifications using dialysis and chromatography (e.g., in S207-S211 of FIG. 2). For example, the exemplary method may further include repeatable purification cycle including dialysis, anion exchange chromatographic process and cation exchange chromatographic process. With the completion of purification processes, the obtained botulinum neurotoxin A may be further filtered and stored at low temperature (e.g., ≤−70° C.) for a long-term storage (e.g., in S213 of FIG. 2).

Each of the exemplary steps in accordance with FIG. 2 may be monitored using different methods, such that the production, extraction and purification of botulinum neurotoxin A as target protein may be realized in controllable manners. Referring back to FIG. 2, for example, acid-mud formation in S203 and flash extraction and dialysis in S205 may be monitored by weighing the precipitate formed with the addition of high concentration of acid, and weighing the precipitate containing ammonium sulfate, respectively. Alternatively, fluorescent assay may be performed to monitor the acid-mud formation. For example, an ultrasensitive fluorescent dye functioning as RiboGreen nucleic acid quantitation reagents may be used for quantitating DNA in aqueous solution, for example, quantitating DNA impurities in an aqueous solution containing proteins. As such, the removal of nucleic acid impurities from the solution containing proteins may be monitored by measuring the reduction in fluorescent intensity of nucleic acids. In some of the optional embodiments, fluorescent assay may be used to monitor the removal of nucleic acid impurities in one or more of steps in FIG. 2, such as in S203 and S205.

In another embodiment of the present disclosure, SDS-PAGE may be used for monitoring the purity of botulinum neurotoxin A for substantially all of the exemplary steps in FIG. 2. Alternatively, UV spectroscopy may also be used for monitoring protein concentration and measuring nucleic acid impurity in the protein solution. For example, the UV absorbance at wavelength of 278 nm may be used to measure and to determine protein concentration. Further, the ratio of UV absorbance at wavelength of 260 nm and 280 nm ($A_{260}/A_{280}$ ratio) may be measured to determine nucleic acid impurity in protein solutions. In addition, qPCR method may also be included to determine the nucleic acid impurity in the solution containing botulinum neurotoxin A, for example, when the concentration of nucleic acid impurity is substantially low. In one embodiment of the present disclosure, TaqMan qPCR assay may be performed to detect residual Type A *Clostridium botulinum* genomic DNA in purified botulinum neurotoxin A sample, thereby ensuring the removal of clostridial DNA impurities from the final product.

It should be noted that one or more methods may be combined to monitor the exemplary steps in FIG. 2. For example, the SDS-PAGE method as well as UV spectroscopy may be combined to monitor the extraction and purification processes, for which the present disclosure will not intend to limit. It should further be noted that other methods may be included in the monitoring of producing and purifying botulinum neurotoxin A, for which the present disclosure is not intended to limit.

For cell inoculation and fermentation (in S201), the preparation of botulinum neurotoxin A with small molecular weight may include preparation of working cell bank (WCB) as well as inoculation and fermentation of the prepared WCB. In one embodiment of the present disclosure, the WCB may be thawed in autoclaved fermentation medium, where the thawing process may be performed at ambient temperature, alternatively, at a temperature of 37° C. Subsequently, the thawed WCB may be inoculated in the autoclaved fermentation medium. In one embodiment, the inoculation process may be carried out for approximately 4 hours to 20 hours in a temperature range of approximately 33° C. to 40° C. For example, the inoculation process may be carried out for 12 hours at a temperature of 37° C.

In some of the optional embodiments of the present disclosure, a master cell bank (MCB) from which bacterium *Clostridium Botulinum* in the WCB may be derived, may be characterized to validate various properties of bacterium *Clostridium Botulinum*. The characterization process may be performed prior to the inoculation and fermentation process, and the characterized properties of bacterium *Clostridium Botulinum* may include identity, biological purity, stability, morphology, DNA sequencing and virus detection when animal-derived ingredients are included in the fermentation process. For example, the identity characterization may be realized by determining phenotypic or genotypic characteristics of the bacterium. The biological activity may be determined by measuring plasma contamination. The stability, defined as consistent production of the intended product of interest, may be determined by nature of the cells, cultivation methods, etc. The viability may be defined as retention of production capacity during storage under defined conditions. It should be noted that some other characteristic properties of the MCB may be identified and measured, for which the present disclosure will not intend to be limiting.

In one embodiment of the present disclosure, during the cell inoculation and fermentation process, it may be preferable to substantially exclude the use of animal-derived ingredients, thereby avoiding the potential contamination of animal sources to the prepared products. As an alternative of commonly used cooked meat medium and other ingredients originated from animal sources used in inoculation and fermentation processes (e.g., N-Z-Amine and glycerin using bovine and porcine starting materials), one embodiment of the present disclosure may include substantially non-animal-derived-ingredient fermentation medium. Another embodiment of the present disclosure may optionally include plant peptone-based fermentation medium.

For example, vegetable-based protein products may be included in the fermentation medium, including, but not limited to, soy, potato and/or rice. Furthermore, autolyzed yeast paste, yeast extract and glucose may also be included in the fermentation medium. In one embodiment of the present disclosure, the non-animal-derived-ingredient fermentation medium may include 5% soy flour, 2% yeast extract, and 2% autolyzed yeast paste by weight over a total volume (w/v) of the medium. Optionally, the non-animal-derived-ingredient fermentation medium may include 3% soy flour, 2% potato flour, 2% yeast extract, and 1% autolyzed yeast paste. Optionally, the non-animal-derived-ingredient fermentation medium may include 3% soy flour, 1% yeast extract, 2% autolyzed yeast paste and 1% glucose. The non-animal-derived-ingredient fermentation medium may further include dextrose and sodium hydroxide (e.g., about 10%-50% aqueous solution) for pH adjustment. In one embodiment, the concentration of dextrose in the fermentation medium may be 5 gram per liter (5 g/L). As used herein, unless otherwise specified, the ingredient percentage described in the present disclosure means a weight percentage over a total volume.

The prepared non-animal-derived-ingredient fermentation medium may be adjusted to an appropriate pH value. In one embodiment, the pH of the fermentation medium may be in a range from pH 6.5 to pH 8.5. For example, the pH of the fermentation medium may be in a range from pH 7.0 to pH 7.5. In some of the optional embodiment, the pH of the fermentation medium may be adjusted to pH 7.2, and the pH value adjustment may be realized by the addition of sodium hydroxide, for example, by adding 0.3 mL of 50% sodium hydroxide into 1 L of the fermentation medium.

With further reference to step S201 of FIG. 2, the working cells in the inoculation solution may be transferred to a greater volume of fermentation medium such that *Clostridium botulinum* may grow and expand in an anaerobic environment. The duration of the fermentation process may be between 70 hours to 120 hours at a temperature range of approximately 33° C. to 40° C. In one embodiment of the present disclosure, the fermentation process may be approximately 96 hours at a temperature range of 35° C. to 39° C. In accordance with the various embodiments, 9 L of the non-animal-derived-ingredient fermentation medium may produce more than 2 billion ($10^9$) mouse $LD_{50}$ units of botulinum neurotoxin A, where each mouse $LD_{50}$ unit may be defined a lethal dose in a mouse $LD_{50}$ assay corresponding to approximately 3-54 picograms of botulinum neurotoxin A.

With reference to step S203 of FIG. 2 in accordance with various embodiments of the present disclosure, the fermentation medium including bacterium *Clostridium botulinum* at harvest may be precipitated to realize acid-mud formation. In one embodiment, high concentration acid may be added to the fermentation medium including bacterium *Clostridium botulinum*, in order to remove cell debris. For example, 3N $H_2SO_4$ may be added into the fermentation medium until the pH was reduced to 3.5 for at least three hours, such that substantially all of the cells may sediment to form precipitate.

In one embodiment of the present disclosure, the precipitate formed by acidification of the fermentation medium may be collected by centrifugation and resuspended for extraction in 100 mM citrate buffer with pH value of 5.5 for a pre-determined time. Meanwhile, the supernatant obtained from centrifugation, containing botulinum neurotoxin A, nucleic acid impurities and other protein impurities, may be collected. In some of the optional embodiments, the centrifugation and resuspension processes may be repeated such that a majority or even substantially all of the botulinum neurotoxin A may be extracted into supernatant. For example, the acidified fermentation medium may be centrifuged for the first time, such that the supernatant may be separated from precipitate. The remaining precipitate may be resuspended in 100 mM citrate buffer for 1 hour for extraction, followed by a second time of centrifugation. Subsequently, the supernatant obtained from the second centrifugation may be separated from precipitate, where the supernatant may be merged with the supernatant obtained from the first centrifugation, and the precipitate may be resuspended for a third time. The merged supernatant may be added with ammonium sulfate for further precipitation. In one embodiment of the present disclosure, the precipitation process of the merged supernatant may be performed for approximately 4-20 hours at a temperature of 2-8° C. In accordance with the aforementioned embodiments, RiboGreen assay and the $A_{260}/A_{280}$ ratio from the UV absorption assay may be performed to monitor the removal of nucleic acid impurities for each cycle of acid precipitation.

With reference to step S205 of FIG. 2 in accordance with various embodiments of the present disclosure, the addition of high concentration of ammonium sulfate into the above supernatant may lead to reduction in solubility of the proteins in the supernatant. When the concentration of ammonium sulfate was sufficiently high, the proteins may precipitate out of the solution. In one embodiment, the precipitant may be collected by centrifugation and resuspended in 50 mM of citrate buffer with a pH value of 5.5. Subsequently, the resuspended precipitate may be further treated to substantially remove nucleic acid impurities and other protein impurities. In one embodiment of the present disclosure, the resuspended precipitate may be mixed with anion exchanger for further extracting botulinum neurotoxin A as target protein, where the anion exchanger may include diethylaminoethyl (DEAE) sephadex A-50 bead slurry. According to some of the optional embodiments, the above extraction processes using anion exchangers may be repeated in order to realize an effective extraction of botulinum neurotoxin A. For example, the resuspended solution in 50 mM of citrate buffer with pH 5.5 may be mixed with DEAE sephadex A-50 bead slurry in a ratio of 1:1 and rocked for 1 hour (1' extraction). The obtained slurry mixture may be centrifuged such that the supernatant may be collected, while the precipitate may be resuspended in 50 mM of citrate buffer with a pH value of 5.5. The resuspended solution may be mixed for with DEAE sephadex A-50 bead slurry in a ratio of 1:1 and rocked for 1 hour ($2^{nd}$ extraction). All of the supernatant after the first and second centrifugation may be merged, and added with ammonium sulfate for further precipitation. In one embodiment of the present disclosure, the precipitation process of the merged supernatant may be performed for approximately 4-20 hours at a temperature of 2-8° C.

As described above, the botulinum neurotoxin complex containing botulinum neurotoxin, associated with other non-toxic proteins such as non-hemagglutinating proteins and hemagglutinins, has a greater molecular weight (e.g., 960 kDa) and is negatively charged. In existing technologies, anion exchange chromatography medium is primarily used for purifying the botulinum neurotoxin complex. In various embodiments of the present disclosure, the produced botulinum neurotoxin A dissociated from other non-toxic proteins may have a significantly smaller molecular weight of 150 kDa. Further, the dissociated botulinum neurotoxin A is positively charged. Accordingly, the present disclosure provides a method for purifying botulinum neurotoxin A using sequential dialysis, anion exchange and cation exchange chromatography. For example, the sequential use of anion exchange chromatography medium and cation exchange chromatography medium may be used to remove substantially all of the remaining nucleic acid impurities, other protein impurities as well as non-toxic proteins dissociated from botulinum neurotoxin A, thereby realizing the purification of positively-charged botulinum neurotoxin A with small molecular weight. In accordance with the aforementioned embodiments, different methods may be utilized to monitor each of the above purification processes. For example, SDS-PAGE method and UV spectroscopy may be both utilized to detect the removal of nucleic acid impurities and other protein impurities.

With reference to step S207 of FIG. 2 according to the embodiments of the present disclosure, the precipitate containing ammonium sulfate obtained from step S205 may be treated with anion resin extraction and dialysis. For example, the precipitate containing ammonium sulfate may be collected by centrifugation and resuspended in 50 mM of citrate buffer with a pH value of 5.5. The resuspended solution may further be dialyzed. In one embodiment of the present disclosure, the resuspended solution may be dialyzed in 50 mM of citrate buffer with a pH value of 5.5, for approximately 4-20 hours at a temperature of 2° C.-8° C. Subsequently, the dialyzed product collected from dialysis tubing may be loaded into DEAE sephadex A-50 column for anion exchange chromatographic process, which may significantly remove negatively-charged nucleic acid impurities and other protein impurities.

In one embodiment of the present disclosure, the dialyzed product collected from dialysis tubing may be weighed prior to get loaded into DEAE sephadex A-50 column. Furthermore, UV spectroscopy may be utilized to monitor the removal of nucleic acid impurities. For example, the collected product with a $A_{260}/A_{280}$ ratio lower than 0.6 may be pooled, where the substantially small $A_{260}/A_{280}$ ratio may indicate lower concentration of nucleic acid impurities. In addition, the pooled product obtained after the anion exchange chromatographic process may also be weighed and compared with the dialyzed product before loading, such that the impurity removal may be operated and monitored in a controllable manner.

The anion exchange chromatographic process may further be repeated to realize effective removal of nucleic acid impurities and other protein impurities, according to the embodiments of the present disclosure accompanied by step S209 of FIG. 2. For example, after the first time of dialysis followed by anion exchange chromatographic process, the product with an $A_{260}/A_{280}$ ratio lower than 0.6 may be pooled and further added with ammonium sulfate for precipitation, which may be performed for approximately 4-20 hours at a temperature of 2° C.-8° C. Subsequently, the precipitate containing ammonium sulfate may be collected by centrifugation and resuspended in 20 mM of phosphate buffer with a pH value of 7.9. The high pH value of 7.9 may result in the dissociation of botulinum neurotoxin A from non-toxic proteins, which may in turn facilitate the purification of small molecular weight botulinum neurotoxin A with subsequent removal of the dissociated non-toxic proteins. The resuspended solution may further be dialyzed. In one embodiment of the present disclosure, the resuspended solution may be dialyzed in 20 mM of phosphate buffer with a pH value of 7.9, for approximately 4-20 hours at a temperature of 2° C.-8° C. Subsequently, the dialyzed product collected from dialysis tubing may further be loaded into DEAE sephadex A-50 column for the second time of chromatographic process which may substantially remove all of the remaining nucleic acid impurities and majority of protein impurities.

With the completion of second time of dialysis and anion exchange chromatography according to the aforementioned embodiments of the present disclosure, the obtained pooled product may further be treated with cation exchange chromatography, which may purify positively-charged botulinum neurotoxin A. For example, the obtained pooled product may be added with ammonium sulfate for further precipitation, which may be performed for approximately 4-20 hours at a temperature of 2° C.-8° C. The precipitate may be collected by centrifugation, resuspended in 20 mM of phosphate buffer with a pH value of 7.0 for a third time of dialysis. In one embodiment of the present disclosure, the resuspended solution may be dialyzed in 20 mM of phosphate buffer with a pH value of 7.0, for approximately 4-20 hours at a temperature of 2° C.-8° C. Subsequently, the dialyzed product collected from dialysis tubing may further be treated for cation exchange chromatographic process. In one embodiment of the present disclosure, a pre-packed SP cation exchange column using a Superloop and a P-50 pump may be utilized to realize the cation exchange chromatographic process.

In one embodiment of the present disclosure, the product obtained after the third time of dialysis may be weighed prior to get loaded into the SP cation exchange column for cation exchange chromatography. Furthermore, in order to monitor the purity as well as to establish an elution profile of botulinum neurotoxin A, the collected products after the cation exchange chromatography may be measured for UV absorbance at wavelength of e.g., 260 nm, 270 nm, 278 nm, 280 nm and 320 nm, respectively. In addition, the pooled product obtained after the cation exchange chromatographic process may also be weighed and compared with the dialyzed product before loading, such that the impurity removal may be operated and monitored in a controllable manner. The purity of botulinum neurotoxin A may further be determined by SDS-PAGE method.

In some of the optional embodiments, the sequential dialysis and chromatography may also be used to purify botulinum neurotoxin A complex with large molecular weight. For example, the 960 KDa BoNT-A may be prepared by dialysis followed by ion exchange chromatography in accordance with e.g., FIG. 2. In particular, a sequential purification process may be performed to prepare for 960 KDa BoNT-A complex, including the steps of dialysis→anion exchange chromatography→dialysis→anion exchange chromatography→dialysis→cation exchange chromatography. It should be noted that to acquire the large molecular weighted BoNT-A complex, the use of phosphate buffer with a pH value of 7.9 may not be needed.

The pooled product collected after the cation exchange chromatographic process, containing high purity of botulinum neurotoxin A, may be stored for long-term use. In one embodiment of the present disclosure, 15% of ethylene glycerol, 3% glycerol and 2% propylene glycol may be added into the pooled product, and the mixture may be stored at temperature lower than or equal to −70° C. Optionally, the product may be stored at −80° C.

Both BoNT-A and holo BoNT-A molecules are large protein compounds with great enzymatic activity which relies on its local micro-environment factors such as pH, presence of other proteins, ionic strength, light, temperature, etc. In some of the optional embodiments, human serum albumin (HSA) or recombinant human albumin (RHA) may be added in toxin solution for purposes of toxin stabilization and long-term storage.

After holo BoNT-A was separated from other associated proteins, it may become relatively less stable compared with BoNT-A complex under a same storage condition, especially when it was diluted for storage or usage afterwards. In one embodiment, one or more of ethylene glycol, glycerol (glycerin) and propylene glycol may be used as a stabilizing agent for stabilizing both BoNT-A complex and holo BoNT-A with small molecular weight. In some of the optional embodiments, the stabilizing agents including one or more of ethylene glycol, glycerol (glycerin) and propylene glycol may have a total concentration of 10%-30%, for example, in a total concentration of 20%-25%. In one embodiment, the stabilizing agents may include ethylene glycol (5-20% by wt.), glycerin (1-10% by wt.) and propylene glycol (1-5% by wt.). In another embodiment, the stabilizing agent may include 10% ethylene glycol, 3% glycerol and 2% propylene glycol.

The present disclosure also provides a method for preparing biomolecules in nano-encapsulation. In some of the optional embodiments, the encapsulated biomolecules may have a broad range of molecular weights. For example, the encapsulated biomolecules may include one or more of bio-molecules with a large molecular weight near or over 1000 KDa such as BoNT-A complex (960 KDa) and hyaluronic acid (≤1500 KDa). In another embodiment, the encapsulated biomolecules may include one or more of bio-molecules with medium molecular weight, including holo BoNT-A (150 KDa) and small molecules including amino acids, proteins, peptides, oligonucleotides, vitamin molecules (e.g., vitamin C and/or vitamin D), Snap-8 octapeptide, di-peptides, allantoin, niacinamide, aloe vera, Co-enzyme Q10, resveratrol, palmitoyl-KTTKS, palmitoyl-GHK, palmitoyl-GQPR, palmitoyl-oligopeptides, aptamers, si-RNAs, stem cells and matrix, stem cells, aptamers, stem cell liquids, variety of cell growth factors such as EGF, FGF, KGF, AGF, BGF, many therapeutic agents such as insulin, celecoxib, rofecoxib, 5-floro-uracil, diacarbazine, ibuprofen, tetracycline, oxytetracycline, estriol, progesterone, doxycycline, minocycline, estradiol, silver ions (e.g., AgNO$_3$), Zn ions (e.g., ZnO), plant extracts, for which the present disclosure is not intended to limit.

Figure 5A:
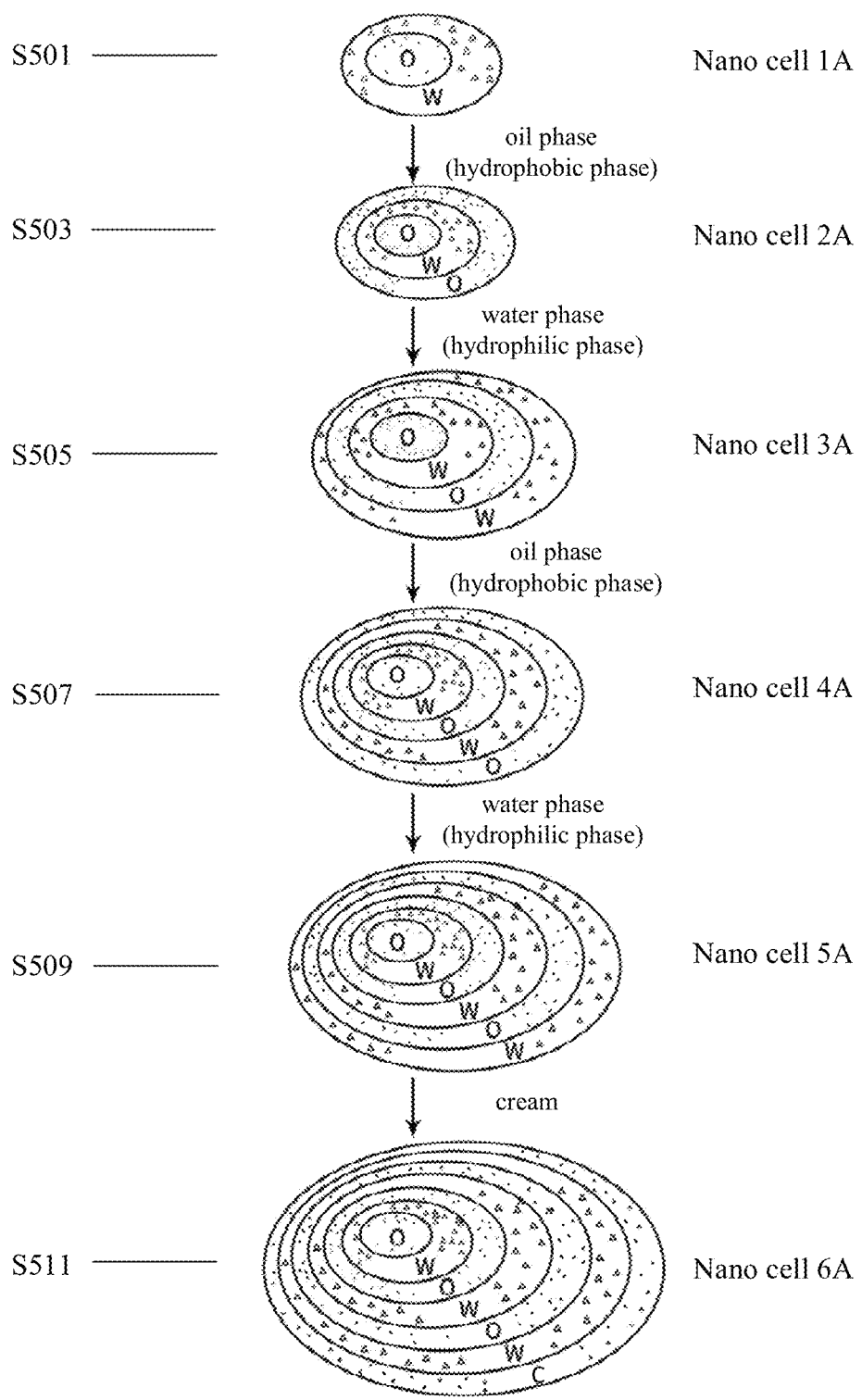
FIG. 5A illustrates a flow chart of an exemplary method for preparing biomolecules in nano-encapsulations according to various embodiments of the present disclosure.

FIG. 5A illustrates a flow chart of an exemplary method for preparing biomolecules in nano-encapsulation according to various embodiments of the present disclosure.

In accordance with S501 of FIG. 5A, nano cell 1A may firstly be formed including an oil phase core wrapped by a water phase layer (also called as oil-in-water (O/W) structure), where water soluble compounds and oil soluble compounds may be dissolved in water phase and oil phase, respectively. The oil-in-water nano cell 1A may be achieved by micelles formation in the presence of amphiphiles with two distinct molecular regions such as a hydrophilic headgroup and a hydrophobic ail, in which the hydrophobic core may represent an oil phase and the hydrophilic shell may represent the water phase.

It should be noted that in the present disclosure, the use of the terms of "water phase" and "hydrophilic phase" may be interchangeable, and the use of the terms of "oil phase" and "hydrophobic phase" may also be interchangeable.

In one embodiment of the present disclosure, a variety of water-soluble compounds may be dissolved in one or more water phase layers within the encapsulated structure, while a variety of oil-soluble compounds may be dissolved in one or more oil phase layers within the encapsulated structure. For example, water-soluble biomolecules (e.g., proteins, peptides, nucleic acids, etc.) may be dissolved in one or more water phase layers within the encapsulated structure, although in some of the optional embodiments, the proteins may have hydrophobic parts included in the oil phase layers. In another embodiment, one or more water phase layers may be dissolved with water-soluble biomolecules while one or more oil phase layers may be dissolved with oil-soluble compounds, thereby forming a nano cell including two or more types of molecules, where the two or more types of molecules may be at least one of hydrophobic and hydrophilic.

In one embodiment, the stirring can be realized through magnetic stirring or mechanical stirring. And the stirring speed may be arranged from 300 rpm-3000 rpm, for example, from 500 rpm-2000 rpm. In some of the embodiments, the stirring speed may be arranged to be approximately 800 rpm.

In another embodiment, a weight ratio of an oil phase to a water phase may be arranged from 1:99 to 40:60, for example, arranged from 5:95 to 20:80. Further in one embodiment, a weight ratio of surfactant to oil in oil phase is from 10:1 to 1:10, for example from 3:1 to 1:3.

In some of the embodiments, oil and surfactants may be used to form the oil phase or used as micelles formation agents, including one or more of Tween-80, Tween-65, Tween-60, Tween-20, Tween-40, Cremophor EL, Labrafac Lipophile WL 1349, soybean oil, tea oil, octanoic acid decanoic acid ester of glycerol, lecithin egg phosphatidylcholine (EPC), PEG-40 hydrogenated castor oil, poly(propyleneoxide) (PPO), poly(D,L-lactic acid) (PDLLA), poly (ε-caprolactone) (PCL), poly(L-aspartate), poloxamers, PEG-polyglutamate, PEG-polyaspartate, PEG-poly-L-lactide, sorbitan oleate (Span-80).

In some of the embodiments, the mixing process may be performed at room temperature (25° C.), or even below room temperature (e.g., 4° C.-25° C.). In another embodiment, the mixing process may be performed at an elevated temperature (e.g., approximately 40° C.). For example, the elevated temperature may be approximately 60° C.-70° C. while not exceeding e.g., 90° C., when heat may be needed to accelerating dissolve of oil phase or water phase. As compared with higher temperature of 50° C.-70° C., the mild preparation process using low manufacturing temperatures (e.g., 4° C.-25° C. or 4° C.-40° C.) may provide additional advantages to the disclosed method especially when a higher temperature may cause the activity loss or retention of encapsulated biomolecules.

According to the aforementioned embodiments, the prepared nano cell 1A having an oil-in-water structures, may further be encapsulated in its opposite polarity phase solution, that is, an oil phase layer, to form nano cell 2A according to S503 of FIG. 5A. The formed nano cell 2A may have a multilayer structure at least including an oil phase core sequentially encapsulated in a water phase layer and another oil phase layer as an outer shell. According to the aforementioned embodiments, each of the oil phase layers may contain a same or different hydrophobic active ingredients, and the water phase core may contain another hydrophilic active ingredients.

In one embodiment in accordance with S505 of FIG. 5A, the above encapsulation steps may be repeated for wrapping additional encapsulating layers containing one or more types of active ingredients in the newly-formed water phase outer shell, to form stable nano cell 3A.

In one embodiment of the present disclosure, the above encapsulation steps may be repeated for a plurality of times in order to form a multi-layer nano cell structure which may mimic the multi-layer human skin structure and human cell structure. Such multi-layer nano cell structure may facilitate the transportation and delivery of active ingredients to inner skin cells. During each encapsulation step according to another embodiment of the present disclosure, the newly formed water phased and oil phased encapsulation layers may contain a same active ingredient molecules as in those in inner layer. Alternatively, the newly formed encapsulating layers may contain different active ingredients, producing multi-functional nano cell with two or more layers containing different active ingredients targeting different therapeutic, cosmeceutical as well as other applications.

In some of the optional embodiments, the formed nano cell 3A having a multilayer structure of oil-water-oil-water layers along a direction from an inner oil phase core to an outer water phase shell, may further be re-encapsulated in an oil phase to obtain nano cell 4A according to S507 of FIG. 5A. In another embodiment, the formed nano cell 4A having a multilayer structure of oil-water-oil-water-oil along a direction from the inner oil phase core to the outer oil phase shell, may further be re-encapsulated in a water phase to obtain nano cell 5A according to S509 of FIG. 5A.

It should be noted that a number of layers in the formed nano cell may be not limited according to the aforementioned embodiments of the present disclosure. That is, a number of layers of hydrophilic phase and a number of layers of hydrophobic phase may be determined according to different applications, for which the present disclosure is not intended to limit. Further, one or more types of active ingredients may be dissolved in one or more of the different phase layers, depending upon the compatibility of the polarity of the active ingredients with the polarity of the layers.

In one embodiment of the present disclosure according to S511 of FIG. 5A, the prepared nano cell 5A may further be wrapped up in a cream to produce nano cell 6A in a stable serum form, where an average particle size of nano cell 6A may be smaller than 50 nm. In one embodiment, the average particle size of nano cell 6A may be smaller than 30 nm. In another embodiment, the average particle size of nano cell 6A may be smaller than 20 nm, or even smaller than 10 nm.

In one embodiment of the present disclosure, the produced nano cell may be wrapped in one or more cream layers. The addition of cream layers may improve the properties of the nano cell in transdermal delivery, as well as in therapeutic and cosmeceutical applications. Further, the cream layers of the produced nano cell may also improve user experience.

Figure 5B:
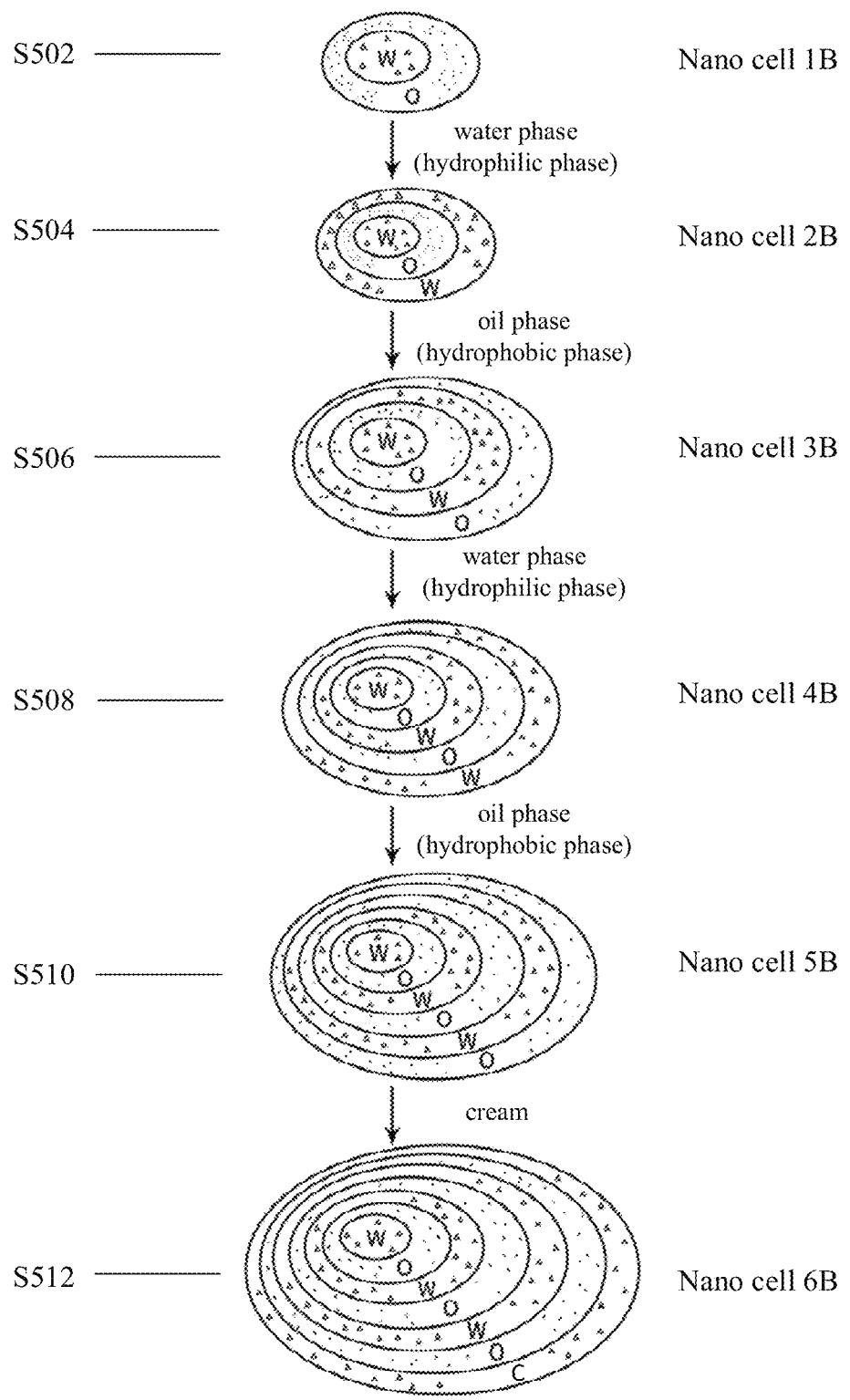
FIG. 5B illustrates a flow chart of another exemplary method for preparing biomolecules in nano-encapsulations according to various embodiments of the present disclosure.

FIG. 5B illustrates a flow chart of another exemplary method for preparing biomolecules in nano-encapsulation according to various embodiments of the present disclosure. In accordance with S502 of FIG. 5B, nano cell 1B may firstly be formed including a water phase core wrapped by an oil phase layer (also called as water-in-oil (W/O) structure), where water soluble compounds and oil soluble compounds may be dissolved in water phase and oil phase, respectively. The nano cell 1B with the water-in-oil structures may be prepared by adding a water phase solution into a stirring oil phase in the presence of surfactants. In one embodiment, the biomolecules e.g., botulinum neurotoxin and/or hyaluronic acid may be dissolved in the water phase core, where the core may be encapsulated in an oil phase layer. In some of the optional embodiments, some proteins may also have hydrophobic parts included in the oil phase layer.

According to the aforementioned embodiments, the prepared nano cell 1B having a water-in-oil structures, may be encapsulated in its opposite polarity phase solution, that is, a water phase layer, to form nano cell 2B according to S504 of FIG. 5B. The formed nano cell 2B may have a multilayer structure at least including a water phase core sequentially encapsulated in an oil phase layer and another water phase layer as an outer shell. Further depending upon the polarity of the outer shell of the nano cell, an additional layer with a different polarity from that of the out shell may be applied. According to S508 of FIG. 5B, for example, an additional water phase layer may be formed to produce nano cell 4B having a multilayer structure of water-oil-water-oil-water along a direction from the inner water core to the outer water shell. In some of the embodiments, the above encapsulation may further be repeated to form nano cell 5B which has a multilayer structure of water-oil-water-oil-water-oil along a direction from the inner water core to the outer oil shell, according to S510 of FIG. 5B.

In one embodiment of the present disclosure according to S512 of FIG. 5B, the prepared nano cell 5B may further be wrapped up in a cream to produce nano cell 6B in a stable serum form, where an average particle size of nano cell 6B may be smaller than 50 nm. In one embodiment, the average particle size of nano cell 6B may be smaller than 30 nm. In another embodiment, the average particle size of nano cell 6B may be smaller than 20 nm, or even smaller than 10 nm.

The addition of cream layer, for which will be described in detail below, may be compatible with the hydrophilic outer shells of nano cell 5A according to S511 of FIG. 5A and the hydrophobic outer shells of nano cell 5B according to S512 of FIG. 5B. It may significantly simplify the manufacture process of adding cream layer as the outer shell of the formed nano encapsulation structures where these structures may have different layer distributions based upon their specific applications. On the other side, the addition of cream layer may stabilize the formed nano encapsulation structures in a serum form, thereby improving the user experience.

As such, various embodiments further include nanoparticles. An exemplary nanoparticle may include an innermost water phase core including biomolecules encapsulated by an oil phase layer, thereby forming a water-in-oil structure; a plurality of water phase layers; a plurality of oil phase layers; and an outmost cream layer. The biomolecules include botulinum neurotoxin and/or hyaluronic acid. Each of the plurality of water phase layers and each of the plurality of oil phase layers alternatively encapsulate the water-in-oil structure. For example, the nanoparticle is a multi-layered nanoparticle and has an average size of less than 50 nanometers, such as in a range of 3 nanometers to 20 nanometers.

In various embodiments, the cream layer may be the outmost layer of the disclosed nanoparticles. For example, the outmost cream layer may include a water phase mixture and an oil phase mixture. In one embodiment, the water phase mixture includes at least one of glycerin, dipotassium glycyrrhizate, propylene glycol, methylparaben and carbomer. The oil phase mixture may include at least one of mineral oil, cetearyl alcohol, propylparaben, methylparaben, PEG-100 stearate, PEG-40 hydrogenated castor oil, caprylic/capric triglyceride, Tween-80, Cremphor EL, glyceryl stearate, Tween-65, Tween-60, Tween-20, Labrafac Lipophile WL 1349, soybean oil, tea oil, vegetable oil, sunflower seed oil, fish oil, sesame oil, vitamin E, animal lipid oil, octanoic acid decanoic acid ester of glycerol, lecithin egg phosphatidylcholine (EPC), poly(propyleneoxide) (PPO), poly(D,L-lactic acid) (PDLLA), poly(ε-caprolactone) (PCL), poly(L-aspartate) and poloxamers, PEG-polyglutamate, PEG-polyaspartate, PEG-poly-L-lactide, PEG derivatives, sorbitane monopalmitate, and sorbitan oleate (Span-80).

EXAMPLES

It should be noted that the described example sets forth some of the aforementioned embodiments of the present disclosure, while having no intention to limit the scope of the present disclosure.

Example 1: Preparation of Botulinum Neurotoxin a Using Non-Animal-Derived-Ingredient Fermentation Medium Example 1 included at least portion of the aforementioned steps illustrated in FIG. 2. In accordance with the detailed description as follows, for upstream process, Example 1 included steps of inoculation and fermentation of working cells using animal derived ingredient-free fermentation medium. For downstream process, Example 1 included acid-mud formation by acidifying the fermentation medium, followed by extraction and dialysis. In order to realize the purification of botulinum neurotoxin A, Example 1 further included the steps of dialysis process and sequential chromatographic processes that were repeatedly performed, where different methods were utilized to monitor these steps.

The working cell bank (WCB) for inoculation and fermentation was derived from a master cell bank (MCB), where the MCB was positively identified as *Clostridium botulinum* Type A with no B, E or tetanus sequences present, using polymerase chain reaction (PCR) detection method with serotype specific primers. In particular, three primer pairs were synthesized with the DNA sequences for *Clostridium botulinum* structural genes encoding types A, B, and E neurotoxins listed in Table 1. The genomic DNA of the MCB cells was isolated from a 24-hour culture of the MCB strain in fermentation medium, further passaged in PPYG (per 500 mL culture medium, 25 g plant phytone peptone, 15 g yeast extract, 5 g autolyzed yeast paste, 5 g glucose) medium and grown an additional 24 hours before DNA isolation. The genomic DNA was isolated using DNeasy Blood & Tissue Kit in a mini spin column format (Qiagen, Inc., Germantown, Md.).

Figure 3:
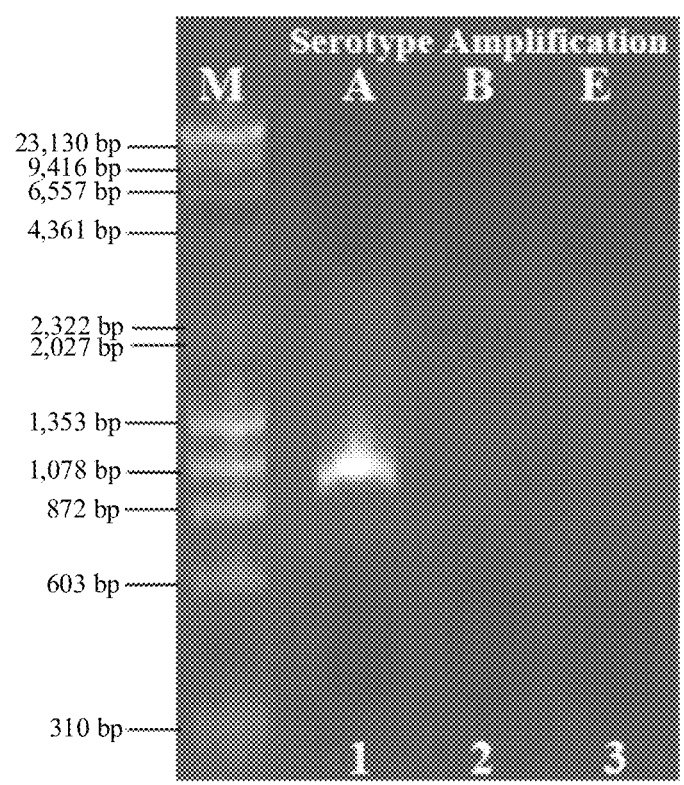
FIG. 3 illustrates results for polymerase chain reaction (PCR) amplification using serotype A DNA samples collected from master cell banks and different serotypes of primers according to various embodiments of the present disclosure.

FIG. 3 illustrates results for PCR amplification using serotype A DNA samples collected from master cell banks and different serotypes of primers according to various embodiments of the present disclosure. As illustrated in FIG. 3, the serotype A PCR amplification product (983 bp) was produced with the Type A primers (Lane 1 in FIG. 3), while no amplification product was produced when serotype B and C primers were used (Lanes 2 and 3 in FIG. 3). Fragment size as shown in Lane M of FIG. 3 was determined by comparison to a lambda DNA HindIII and X174 HaeIII digest marker mix (New England Biolabs, Inc., Ipswich, Mass.). Furthermore, Blast analysis of the serotype specific (neurotoxin) sequence data indicated that each sample produced an amplification product of correct size only in the presence of corresponding serotype specific primers, and the sequences of the serotype A amplification product matched Hall Strain Clostridium botulinum Type A.

TABLE 1

Botulinum Typing PCR Primers.

| VNTR # | Direction | Primer Pair (forward & reverse) |
|---|---|---|
| Type A | Forward | 5'-GTG ATA CAA CCA GAT GGT AGT TAT AG-3' |
|  | Reverse | 5'-AAA AAA CAA GTC CCA ATT ATT AAC TTT-3' |
| Type B | Forward | 5'-GAG ATG TTT GTG AAT ATT ATG ATC CAG-3' |
|  | Reverse | 5'-GTT CAT GCA TTA ATA TCA AGG CTG G-3' |
| Type E | Forward | 5'-CCA GGC GGT TGT CAA GAA TTT TAT-3' |
|  | Reverse | 5'-TCA AAT AAA TCA GGC TCT GCT CCC-3' |

After the validation of MCB cell lines, the cell lines of WCB were derived from MCB cell lines and inoculated into 10 mL of autoclaved non-animal-derived-ingredient fermentation medium for at least overnight at 37° C. The main components of the non-animal-derived-ingredient fermentation medium are listed in Table 2. With the completion of inoculation, 5 mL of the inoculate was used to seed in 9 L of non-animal-derived-ingredient fermentation medium, where the seeding was performed for 96 hours in a temperature range of 35° C. to 39° C.

TABLE 2

Main components of the non-animal-derived-ingredient fermentation medium.

| Medium Ingredients | Percentage (w/v) |
|---|---|
| Plant Phytone Peptone | 5% |
| Yeast Extract | 3% |
| Autolyzed Yeast Paste | 1% |
| Dextrose | 1% |
| Other ingredients | 1% |

For subsequent acid-mud formation process after fermentation, 3N $H_2SO_4$ was added to the fermentate at harvest until a target pH of 3.5 was achieved, such that the working cells were allowed to sediment for a minimum of 3 hours to form precipitate. The precipitate was collected by centrifugation, and resuspended in 100 mM citrate buffer, pH 5.5 for the first time of acid precipitate extraction (1' acid precipitation). The resuspended solution was further centrifuged. The obtained supernatant was decanted and saved, while the remaining precipitate was resuspended in 100 mM of citrate buffer for the second acid precipitate extraction ($2^{nd}$ acid precipitation). The resuspended solution was centrifuged for a third time, and the obtained supernatant was decanted and saved. The two supernatants obtained from the first and second acid precipitation were merged and subsequently, were added with ammonium sulfate for further precipitation overnight at a refrigerated temperature.

During the first and second acid precipitation processes, the nucleic acid impurities were monitored using RiboGreen Assay and UV spectroscopy for measuring a ratio of absorbance at wavelength of 260 nm and 280 nm ($A_{260}/A_{280}$ ratio), such that each step of precipitation and extraction were operated and monitored in a controllable manner. Table 3 lists quantification of nucleic acid impurities included in the extracted solutions. For example, sample ID 1 "acid precipitate extract #1" lists the concentration of nucleic acid impurities after $1^{st}$ acid precipitation (359.3 μg/mg protein), and sample ID 2 "merged acid precipitate extract #1 and #2" lists the concentration of nucleic acid impurities in the merged supernatant after $2^{nd}$ acid precipitation (514.0 μg/mg protein). Table 4 further lists UV $A_{260}/A_{280}$ ratio measured after each step of extraction and purification in Example 1. For example, sample ID 1 "acid precipitate extract #1" lists a $A_{260}/A_{280}$ ratio of 1.54 after $1^{st}$ acid precipitation, and sample ID 2 "merged acid precipitate extract #1 and #2" lists the concentration of nucleic acid impurities in the merged supernatant after $2^{nd}$ acid precipitation (514.0 μg/mg protein).

TABLE 3

Determination of nucleic acid impurities using RiboGreen assay.

| Sample ID | Sample Description | RiboGreen Assay (μg/mg protein) | Total nucleic acid(mg) |
|---|---|---|---|
| 1 | Acid precipitate extract #1 | 386.5 | 359.3 |
| 2 | Merged acid precipitate extract #1 and #2 | 375.3 | 514.0 |
| 3 | Extract resuspended after ammonium sulfate precipitation | 1415.3 | 408.3 |
| 4 | $1^{st}$ DEAE A50 slurry | 189.1 | 40.4 |
| 5 | $2^{nd}$ DEAE A50 slurry | 91.4 | 3.8 |
| 6 | $1^{st}$ DEAE A50 load | 82.8 | 38.5 |

For the subsequent flash extraction and dialysis step, the merged supernatant obtained from the first and second acid precipitation was added with ammonium sulfate for further precipitation. The precipitate was collected by centrifugation and resuspended in freshly-prepared 50 mM citrate buffer, pH 5.5. As shown in Table 3 and Table 4, sample ID 3 "Extract resuspended after ammonium sulfate precipitation" listed the nucleic acid impurities concentration and the $A_{260}/A_{280}$ ratio in the extracted solution after the addition of ammonium sulfate and centrifugation. The extract was further mixed with DEAE Sephadex A-50 bead slurry in a ratio of 1:1 and rocked for one hour ($1^{st}$ DEAE A50 slurry). The obtained first slurry mixture was then centrifuged. The supernatant for the $1^{st}$ DEAE A50 slurry was decanted and saved, while the remaining precipitate was further resuspended with freshly-prepared 50 mM citrate buffer, pH 5.5, and added with DEAE Sephadex A-50 bead slurry in a ratio of 1:1 and rocked for one hour ($2^{nd}$ DEAE A50 slurry). After that, the second slurry mixture was centrifuged, and the obtained supernatant was decanted and saved. The two supernatants obtained from the first and second acid precipitation were merged, and were subsequently added with ammonium sulfate for further precipitation overnight at a refrigerated temperature.

TABLE 4

Determination of nucleic acid impurities using $A_{260}/A_{280}$ ratio measured by UV spectroscopy.

| Sample ID | Sample solution | $A_{260}/A_{280}$ Ratio |
|---|---|---|
| 1 | Acid precipitate extract #1 | 1.54 |
| 2 | Merged acid precipitate extract #1 and #2 | 1.55 |
| 3 | Extract resuspended after ammonium sulfate precipitation | 1.61 |
| 4 | $1^{st}$ DEAE A50 slurry | 1.21 |
| 5 | $2^{nd}$ DEAE A50 slurry | 1.16 |
| 6 | Bulk DEAE A-50 eluent before dialysis | 1.21 |
| 7 | $1^{st}$ DEAE A50 load | 1.2 |
| 8 | $1^{st}$ DEAE A-50 pool | 0.48 |
| 9 | $2^{nd}$ DEAE A50 load | 0.47 |
| 10 | $2^{nd}$ DEAE A-50 pool | 0.47 |
| 11 | SP (Sulfopropyl) load | 0.48 |
| 12 | SP Pool (final product without glycerol) | 0.47 |
| 13 | SP Pool (final product with glycerol) | 0.48 |

As shown in Table 3 and Table 4, the concentration of nucleic acid impurities was monitored during each step of extraction. It was found that the addition of DEAE Sephadex A-50 bead slurry significantly removed nucleic acid impurities. As shown in Table 3, for example, sample ID 4 "$1^{st}$ DEAE A50 slurry" showed significantly reduced concentration of nucleic acid impurities as compared to sample ID 3 "extract resuspended after ammonium sulfate precipitation". Furthermore, the repeatable addition of DEAE A50 bead slurry for extraction effectively removed remaining nucleic acid impurities, by comparing e.g., the nucleic acid impurities concentration of 189.1 μg/mg protein in sample ID 4 "$1^{st}$ DEAE A50 slurry" with 91.4 μg/mg protein in sample ID 5 "$2^{nd}$ DEAE A50 slurry".

It should be noted that RiboGreen assay was used in early stages of extraction and purification processes including steps of acid-mud formation, as well as flash extraction with the use of DEAE Sephadex A-50 bead slurry. After the nucleic acid impurities were substantially removed in the above steps, the relative high concentration of proteins may result in the interference in RiboGreen assay. Hence, other methods including measurement of $A_{260}/A_{280}$ ratio by UV spectroscopy as well as SDS-PAGE were used for monitoring the subsequent extraction and purification processes.

With the completion of flash extraction by repeatable addition of DEAE A50 bead slurry, the obtained product was treated with dialysis and sequential chromatographic processes for removing remaining nucleic acid impurities, other protein impurities as well as non-toxic proteins dissociated from botulinum neurotoxin A, in order to produce small molecular weight botulinum neurotoxin A with high purity.

Figure 4:
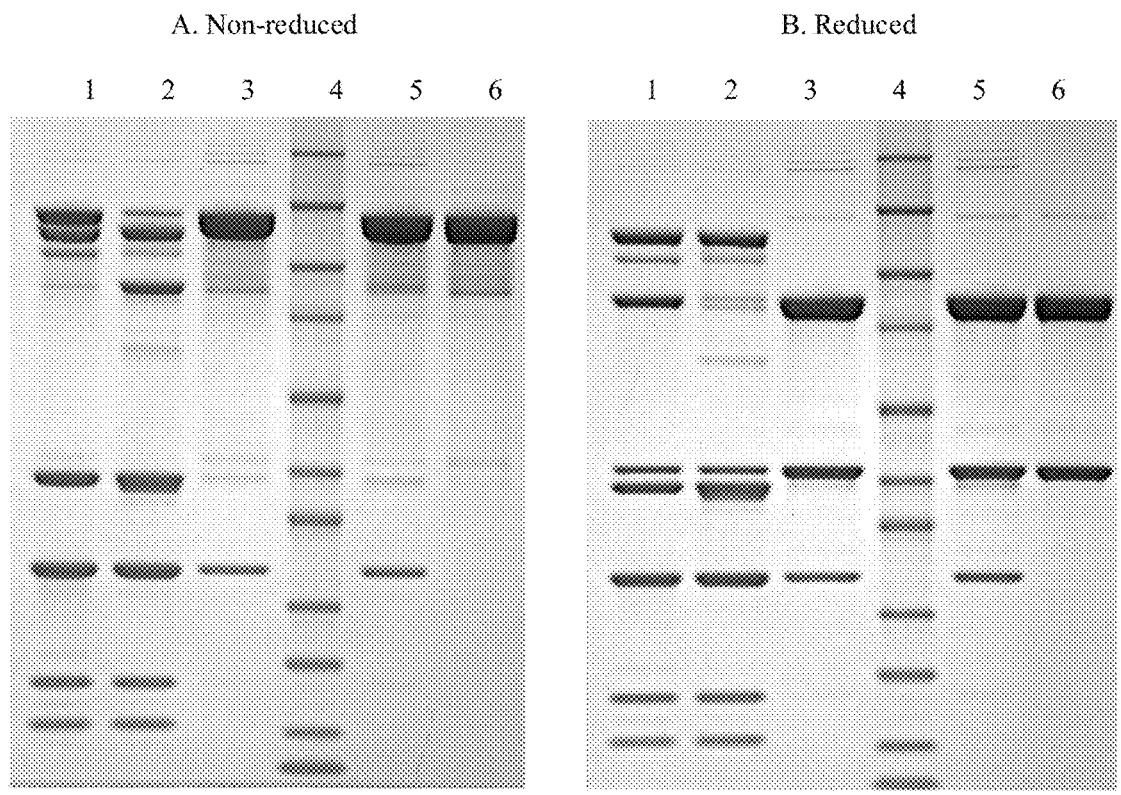
FIG. 4 illustrates sodium dodecyl sulfate polyacrylamide gel electrophoresis (SDS-PAGE) results in accordance with different steps of purification processes in an exemplary method for preparing botulinum neurotoxin A with small molecular weight according to various embodiments of the present disclosure.

In particular, the precipitate containing ammonium sulfate was collected by centrifugation and resuspended in 50 mM citrate buffer, pH 5.5. After that, the resuspended solution was transferred into a dialysis tubing for further removal of nucleic acid impurities in 50 mM citrate buffer, pH 5.5. The dialysis process was performed overnight at a refrigerated temperature ($1^{st}$ dialysis). The obtained product after the first dialysis was loaded into DEAE Sephadex A-50 column for a first time of anion exchange chromatography ($1^{st}$ anion exchange). FIG. 4 illustrates SDS-PAGE results in accordance with each step of sequential chromatographic processes for botulinum neurotoxin A purification. For example, FIG. 4A and FIG. 4B show the SDS-PAGE results monitoring the proteins included during each step of chromatographic processes under non-reduced and reduced conditions, respectively. Lane 1 "$1^{st}$ A-50 Pool" in FIG. 4A and FIG. 4B indicate protein bands existing in the pooled sample after the first anion exchange chromatographic process. The first dialysis and anion exchange process substantially removed any remaining nucleic acid impurities and other protein impurities that were negatively-charged. The collected product after the first anion exchange chromatography having an A260/280 ratio lower than 0.6 was pooled for a second time of dialysis followed by another anion exchange chromatographic process. As shown in Table 4, for example, sample ID 8 "$1^{st}$ DEAE A-50 pool" had an A260/280 ratio of 0.48.

With the completion of $1^{st}$ dialysis and $1^{st}$ anion exchange chromatographic process, the pooled product was added with ammonium sulfate for precipitation. The obtained precipitate was collected by centrifugation and resuspended in 20 mM phosphate buffer, pH 7.9. Under weakly basic condition with pH 7.9, botulinum neurotoxin A with small molecular weight may dissociate from the botulinum neurotoxin complex containing non-toxic proteins. The resuspended solution was transferred into a dialysis tubing in 50 mM citrate buffer, pH 7.9. The dialysis process was performed overnight at a refrigerated temperature ($2^{nd}$ dialysis). The obtained product after the second dialysis was loaded into DEAE Sephadex A-50 column for a second time of anion exchange chromatography ($2^{nd}$ anion exchange). As shown in FIG. 4, the use of citrate buffer with pH 7.9 effectively dissociated botulinum neurotoxin A from non-toxic proteins, which were substantially removed during the second anion exchange chromatographic process, by comparing the loaded sample prior to $2^{nd}$ anion exchange (LANE 3) and the pooled sample after $2^{nd}$ anion exchange (LANE 4). Similarly, the collected product after the second anion exchange chromatographic process having an $A_{260/280}$ ratio lower than 0.6 was pooled. As shown in Table 4, for example, sample ID 10 "$2^{nd}$ DEAE A-50 pool" had an $A_{260/280}$ ratio of 0.47.

As compared to a single step of anion exchange chromatographic process, the repeatable dialysis-anion exchange cycles as described above, substantially removed all of the nucleic acid impurities and a majority of protein impurities from the product. For example, as illustrated in FIG. 4, LANE 1 (1' A-50 pool) which showed the collected product from the $1^{st}$ anion exchange process was compared with LANE 3 ($2^{nd}$ A-50 pool) which showed the collected product from the $2^{nd}$ anion exchange process. A substantial amount of protein impurities were removed after the repeatable anion exchange process.

Since botulinum neurotoxin A is a small molecular weight protein with positive charges under the process condition, the example described herein further included a cation exchange chromatographic process to obtain botulinum neurotoxin A with high purity. Specifically, with the completion of $2^{nd}$ dialysis and $2^{nd}$ anion exchange chromatographic process, the pooled product was added with ammonium sulfate for precipitation. The obtained precipitate was collected by centrifugation and resuspended in 20 mM phosphate buffer, pH 7.0. The resuspended solution was transferred into a dialysis tubing for further removal of any remaining non-toxic proteins in 20 mM phosphate buffer, pH 7.0. The dialysis process was performed overnight at a refrigerated temperature ($3^{rd}$ dialysis). The obtained product after the third dialysis was loaded into pre-packed SP column using a Superloop and a P-50 pump for cation exchange chromatography. As shown in FIG. 4, after the cation exchange chromatographic process, the pooled product showed a clear protein band having a molecular weight of 150 kDa (see e.g., LANE 6 of FIG. 4A). Further, the obtained botulinum neurotoxin A included 100 kDa heavy chain and 50 kDa light chain (see e.g., LANE 6 of FIG. 4B). Hence, the cation exchange chromatographic process using SP columns as described above, effectively purified botulinum neurotoxin A with small molecular weight.

Unlike the botulinum neurotoxin complex having a greater molecular weight (e.g., 960 kDa), the produced botulinum neurotoxin A with small molecular weight according to the aforementioned embodiments of the present disclosure may possess a variety of advantages. For example, botulinum neurotoxin A with molecular weight of approximately 150 kDa, only has less than 20% weight compared to the botulinum neurotoxin complex. As such, the botulinum neurotoxin A may have significantly reduced antigenicity and immunogenicity. Compared to the larger molecular weight complex, the produced botulinum neurotoxin A may be significantly safer for clinical use. Furthermore, due to the small size of the produced botulinum neurotoxin A, it may have higher diffusion rate which makes it easier to be delivered across skin barriers in variety of applications (e.g., local and topical applications), avoiding invasive delivery methods such as needle injection.

Additionally, the produced botulinum neurotoxin A according to the various embodiments of the present disclosure may have a biological molecular activity from 200-400 units per nanogram, e.g., higher than 300 $LD_{50}$ units per nanogram. Compared to botulinum neurotoxin complex having the biological molecular activity of 20 $LD_{50}$ per nanogram, the activity of the produced botulinum neurotoxin A may achieve more than 15 times higher potency. To realize the same treatment effect during clinical use, the amount of the produced botulinum neurotoxin A required may be 15 times less as compared to botulinum neurotoxin complex with larger molecular weight, bring significantly less toxicity to patients.

More importantly, according to the aforementioned embodiments of the present disclosure, the preparation of botulinum neurotoxin A with small molecular weight may not include animal-derived ingredients (e.g., cooked meat medium or glycerin originated from animal source). As such, the safety during the preparation process may be significantly improved, avoiding potential contamination from animal sources to the prepared botulinum neurotoxin A product.

Furthermore, according to the aforementioned embodiments of the present disclosure, the preparation of botulinum neurotoxin A including two chromatographic processes using anion exchange chromatography medium and one chromatographic processes using cation exchange chromatography medium may improve the efficiency of the preparation process. For example, approximately 10-50 mg of botulinum neurotoxin A may be produced by the use of 9 L fermentation medium. The preparation process may be readily scaled up for manufacturing botulinum neurotoxin A with large quantity.

It should be noted that Example 1 was not intended to limit any scope of the present disclosure. In accordance with some of the aforementioned embodiments, the disclosed method in Example 1 may also be used to prepare BoNT-A complex with large molecular weight (e.g., 960 KDa), with modifications in the purification process, for example, the use of buffer solutions with a pH value lower than 7 during the dialysis and chromatographic processes.

Example 2: Preparation of Botulinum Neurotoxin a in Nano-Encapsulation and Transdermal Delivery Example 2 described a preparation process for botulinum neurotoxin A nano-encapsulation. It should be noted that in this example, holo BoNT-A with small molecular weight (e.g., 150 KDa) was used to prepare nano-encapsulation. Alternatively, the large molecular weighted BoNT-A complex may also be used to prepare nano-encapsulation, for which the present disclosure is not intended to limit.

Toxin Nano Cell 1 Preparation

Figure 6:
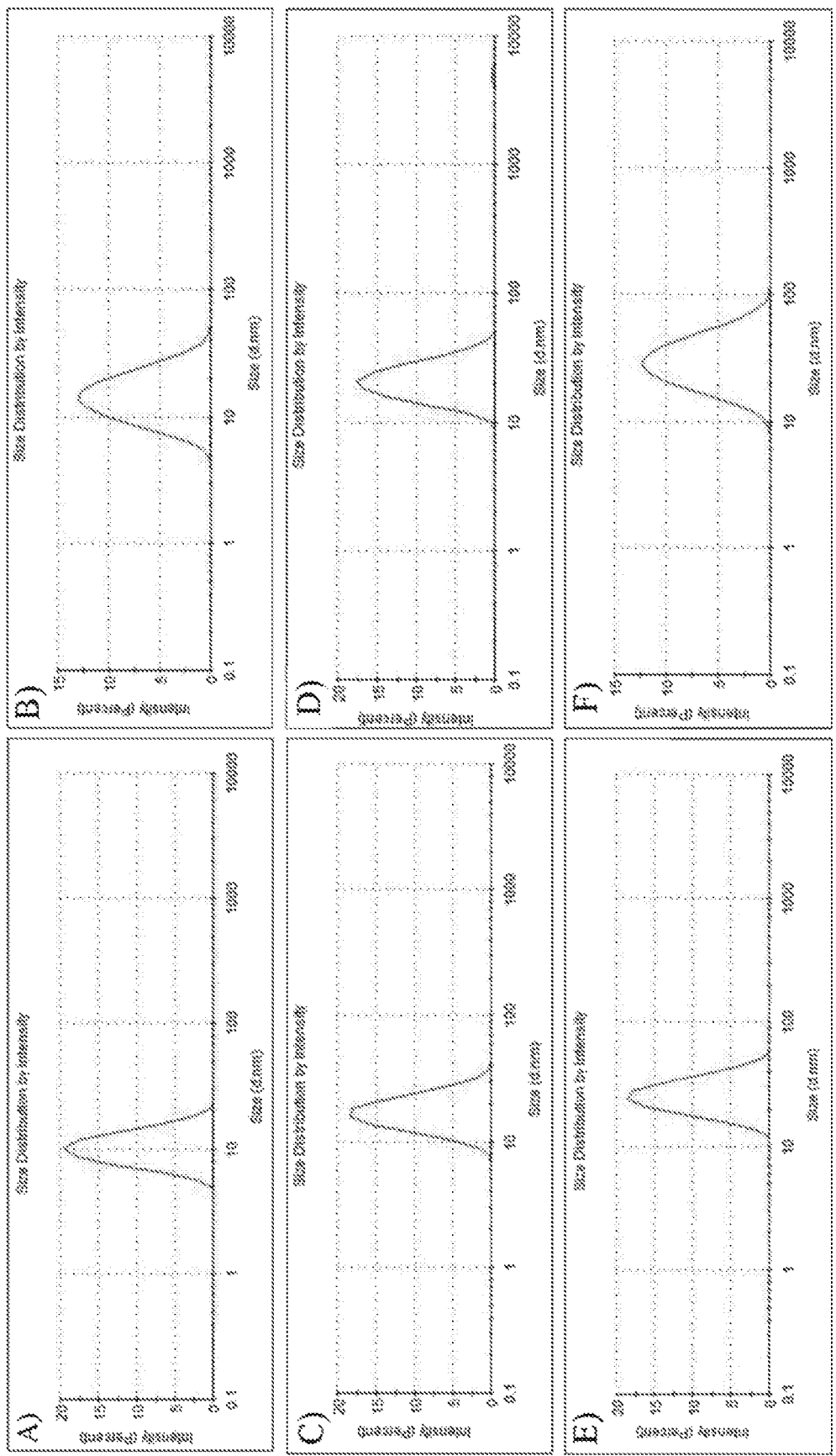
FIG. 6 illustrates particle size and distribution of nano cell encapsulated with botulinum neurotoxin using an exemplary method for preparing botulinum neurotoxin in nano-encapsulation according to various embodiments of the present disclosure.

Active ingredients including biomolecules, e.g., holo BoNT-A may be encapsulated into nanometer-sized cells or emulsions to form toxin nano cell. To prepare toxin nano cell 1 (e.g., S501 of FIG. 5A or S502 of FIG. 5B), 73 mg Tween-80 was added into 10 g stirring aqueous toxin working solution containing holo BoNT-A biomolecules with a potency of 1000 units (LD50) per gram (1000 units/g). The toxin working solution was prepared by serial dilution of holo BoNT-A stock solution with the use of phosphate buffer (20 mM, pH 6.8 containing with 10% ethylene glycol, 3% glycerol and 2% propylene glycol) at room temperature. The stirring of the mixture of Tween-80 and aqueous toxin working solution was kept for approximately 15 minutes until a clear solution was formed. The resulting clear solution including toxin nano cell 1 was measured for particle size and zeta potential on a particle size analyzer (Malvern Panalytical Technologies, Westborough, Mass.). FIG. 6A and Table 5 illustrate size distribution of toxin nano cell 1 by intensity and particle size distribution of toxin nano cell 1 by volume. As can be seen, an average particle size was 9.79 nm by intensity (z average). Furthermore, the size of toxin nano cell 1 by volume distribution, was distributed from 6.96 nm (at 10% accumulative volume) to 14.90 nm (at 90% accumulative volume).

It should be noted that the above preparation of toxin nano cell 1 with an oil-in-water structures was for exemplary purposes only. Alternatively, the holo BoNT-A may be included in water phase core encapsulated by an oil phase layer according to S502 of FIG. 5B, for which the present disclosure is not intended to limit. When the holo BoNT-A was included in the structures of nano cell 1B, that is, in the water phase core of the nano cell, the following repeatable encapsulation steps may also be adjusted accordingly, thereby ensuring each newly formed outer layer having a different polarity from the polarity of the current out layer before the encapsulation process.

Toxin Nano Cell 2 Preparation

Caprylic/capric triglyceride (10 g) was added into PEG-40 hydrogenated castor oil (20 g) in a separate container and mixed well at approximately 40° C. and cooled down to room temperature. After that, 0.5 gram of prepared toxin nano cell 1 prepared from the above process was added in the above mixture and kept stirred for approximately 15 minutes, until a clear solution containing toxin nano cell 2 was formed. The solution was measured for particle size and zeta potential using the particle size analyzer. As illustrated in FIG. 6B and Table 5, an average particle size of toxin nano cell 2 was 12.82 nm by intensity (z average) and the particle size was distributed from 8.27 nm to 25.30 nm by volume distribution.

Toxin Nano Cell 3 Preparation

To prepare toxin nano cell 3, 5 grams of toxin nano cell 2 obtained from the above process was added into 45 grams of toxin working solution (with a potency of 1000 units/g). The mixture was further stirred at a speed of approximately 1000 rpm at room temperature (e.g., 25° C.) for approximately 15 minutes until a bluish transparent solution was formed. The resulted solution containing toxin nano cell 3 (also called nanoparticles or nanoemulsions) was measured for particle size and zeta potential. As illustrated in FIG. 6C and Table 5, an average particle size of toxin nano cell 3 was 16.21 nm by intensity (z average) and the particle size was distributed from 11.40 nm to 25.40 nm by volume distribution.

Toxin Nano Cell 4 Preparation

The preparation of toxin nano cell 4 were similar to the above preparation of toxin nano cell 2. In particular, PEG-40 hydrogenated castor oil (20 g) and caprylic/capric triglyceride (10 g) were mixed well at about 40° C. in a container and cooled down to room temperature. The mixture was added into the toxin nano cell 3 prepared from the above process (0.5 g) with stirring. The mixture was kept stirred for approximately 15 minutes until a clear solution containing toxin nano cell was obtained. The resulted clear solution was measured for particle size and zeta potential. As illustrated in FIG. 6D and Table 5, an average particle size of toxin nano cell 4 was 20.00 nm by intensity (z average) and the particle size was distributed from 13.80 nm to 31.90 nm by volume distribution.

Toxin Nano Cell 5 Preparation

The preparation of toxin nano cell 5 were similar to the above preparation of toxin nano cell 3. In particular, 5 grams of toxin nano cell 4 prepared from the above process was added into 45 grams of toxin working solution (with a potency of 1000 units/g). The mixture was further stirred at a speed of approximately 1000 rpm at room temperature for approximately 15 minutes until a bluish transparent solution was formed. The resulted bluish transparent solution containing toxin nano cell 5 was measured for particle size and zeta potential. As illustrated in FIG. 6E and Table 5, an average particle size of toxin nano cell 5 was 24.53 nm by intensity (z average) and the particle size was distributed from 17.30 nm to 37.70 nm by volume distribution.

Toxin Nano Cell 6 Preparation

Cream 1 was firstly prepared in accordance with the components listed in Table 6. In particular, the components listed as "Phase 1 in Container 1" and the components listed as "Phase 2 in Container 2" were prepared, heated to approximately 70° C. and kept stirred separately, until all of components in the containers were dissolved. After that, the dissolved components in Container 2 was transferred into Container 1 under stirring at approximately 70° C. for about 15 minutes. The mixed components were further cooled down to room temperature to form Cream 1.

TABLE 5

Particle Size and Distribution of Toxin Nano Cell

| Toxin Nano Cell | Average Particle Size (nm) by Intensity | Particle Size (nm) by Volume Distribution (10% Accumulative Volume) | Particle Size (nm) by Volume Distribution (90% Accumulative Volume) |
| --- | --- | --- | --- |
| Toxin Nano Cell 1 | 9.794 | 6.96 | 14.9 |
| Toxin Nano Cell 2 | 12.82 | 8.27 | 25.3 |
| Toxin Nano Cell 3 | 16.21 | 11.4 | 25.4 |
| Toxin Nano Cell 4 | 20.00 | 13.8 | 31.9 |
| Toxin Nano Cell 5 | 24.53 | 17.3 | 37.7 |
| Toxin Nano Cell 6 | 25.84 | 16.3 | 53.1 |

When the formed Cream 1 was cooled down to approximately 50° C., one gram of the Cream 1 was added into the stirring toxin nano cell 5 prepared from the above process in a separate container at room temperature. The mixture was kept stirred for approximately 15 minutes, until the toxin nano cell 6 (also called as nano toxin product) was formed. The formed bluish toxin nano cell 6 was then measured for particle size and zeta potential. As illustrated in FIG. 6F and Table 5, an average particle size of toxin nano cell 6 was 25.84 nm by intensity (z average) and the particle size was distributed from 16.30 nm to 53.10 nm by volume distribution.

TABLE 6

Composition of Cream 1

| | Ingredients | Amount (g) |
| --- | --- | --- |
| Container 1 (Phase 1) | Water | 86 |
| | Glycerin | 6 |
| | Dipotassium glycyrrhizate | 2 |
| | Propylene glycol | 1 |
| | Methylparaben | 0.1 |
| | Carbomer | 0.1 |
| Container 2 (Phase 2) | Mineral oil | 1 |
| | Cetearyl alcohol | 3 |
| | Propylparaben | 0.1 |
| | PEG-100 stearate | 0.35 |
| | Glyceryl stearate | 0.35 |

Thermal Stability of Toxin Nano Cell 6

The prepared toxin nano cell 6 according to the above processes were further tested for stability for a test period of e.g., 180 days, under different storage conditions, including freeze-thaw cycles, frozen conditions (e.g., −20° C.), refrigerated conditions (e.g., 2-8° C.) and room temperature (e.g., 25° C.), respectively. Table 7 lists an average particle size of toxin nano cell 6 and size change during each freeze thaw cycle. Further, Table 8 lists an average particle size of toxin nano cell 6 and size change during different thermal conditions. As can be seen, the prepared toxin nano cell 6 showed good stability with relatively small size change over a testing period of 6 months, under different thermal conditions during storage, including multiple freeze-thaw cycles, 2° C.-8° C. refrigerated storage condition, frozen storage condition (e.g., −20° C.), room temperature (e.g., 25° C.). With the above comparison of different thermal conditions for storage, the toxin nano cell 6 were stored under a low temperature (e.g., −20° C.) to avoid bioactivity loss.

TABLE 7

Thermal Stability of Toxin Nano Cell 6 During Freeze Thaw Cycles

| Freeze Thaw Cycle | Temp. (° C.) | Toxin Nano Cell Particle Size (nm) | Size Change (%) |
| --- | --- | --- | --- |
| Time Zero (initial) | RT (e.g., 25° C.) | 25.84 | 0.0 |
| 1$^{st}$ Cycle | −20° C. | 26.51 | 2.6 |
| 2$^{nd}$ Cycle | −20° C. | 27.87 | 7.9 |
| 3$^{rd}$ Cycle | −20° C. | 27.08 | 4.8 |

TABLE 8

Thermal Stability of Toxin Nano Cell 6

| Storage Temperature | Days of Storage | Particle Size (nm) | Size Change (%) |
| --- | --- | --- | --- |
| Frozen Condition (e.g., −20° C.) | 0 | 25.84 | 0.0 |
| | 7 | 24.79 | −0.7 |
| | 14 | 25.66 | 1.4 |

TABLE 8-continued

Thermal Stability of Toxin Nano Cell 6

| Storage Temperature | Days of Storage | Particle Size (nm) | Size Change (%) |
|---|---|---|---|
| | 28 | 26.19 | 1.4 |
| | 60 | 26.51 | 2.6 |
| | 90 | 27.05 | 4.7 |
| | 180 | 27.62 | 6.9 |
| Refrigerated Condition (e.g., 5° C.) | 0 | 25.84 | 0.0 |
| | 7 | 25.45 | −1.5 |
| | 14 | 25.51 | −1.3 |
| | 28 | 27.65 | 7.0 |
| | 60 | 28.28 | 9.4 |
| | 90 | 28.61 | 10.7 |
| | 180 | 28.74 | 11.2 |
| Room Temperature (e.g., 25° C.) | 0 | 25.84 | 0.0 |
| | 7 | 27.18 | 5.2 |
| | 14 | 26.5 | 2.6 |
| | 28 | 26.51 | 2.6 |
| | 60 | 28.35 | 9.7 |
| | 90 | 29.41 | 13.8 |
| | 180 | 29.56 | 14.4 |

Therapeutic and Cosmeceutical Applications Using Toxin Nano Cell 6

Figure 7:
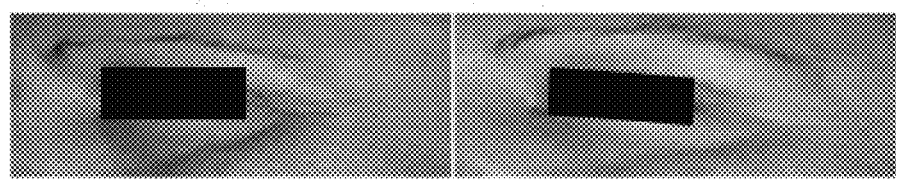
FIG. 7 illustrates comparisons of skin areas of patients applied with nano cell encapsulated with botulinum neurotoxin according to various embodiments of the present disclosure.
Figure 7:
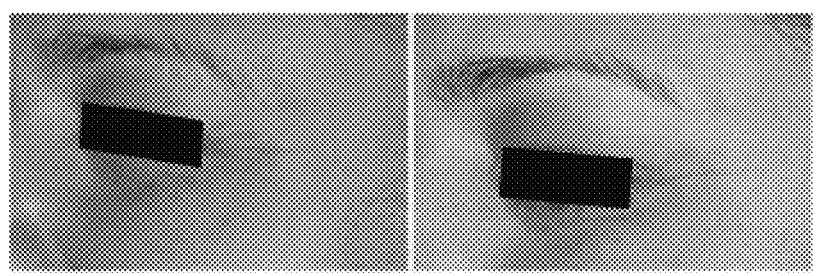
Figure 7:
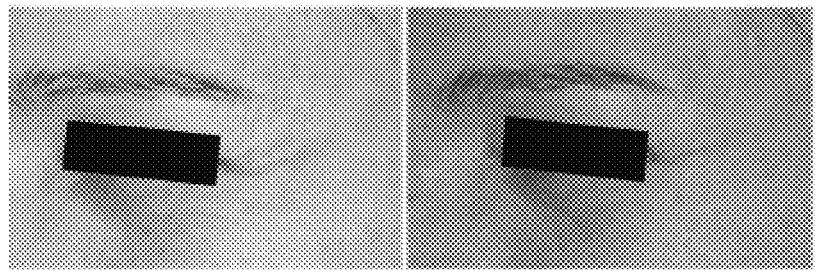
Figure 7:
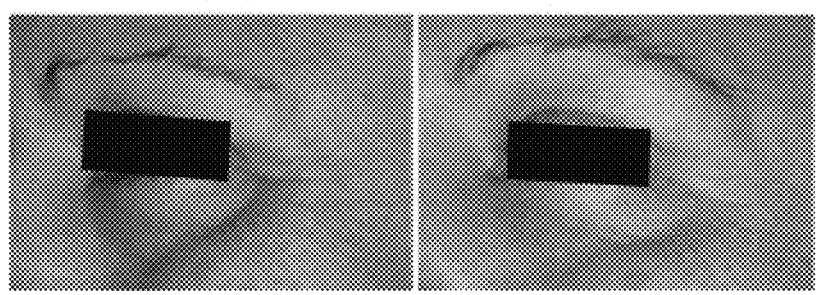

The prepared toxin nano cell 6 were prepared in a form of serum and tested on facial areas of patients in therapeutic and cosmeceutical applications. In particular, the facial areas of each patient before applying the toxin nano cell 6 were recorded via color images. After that, approximately 0.2 mL serum containing the toxin nano cell 6 prepared from the above processes was applied to only one side of the cross-feet facial areas for once. The observations were sequentially performed and recorded at the time duration of 1 week, 2 weeks, and 4 weeks, respectively. FIG. 7 illustrates comparisons of facial areas of patients applied with the prepared botulinum neurotoxin A in nano-encapsulation according to various embodiments of the present disclosure. As can be seen, relaxation and reduction of wrinkle lines on the facial area treated with topical application using toxin nano cell 6 was already visible after 2 weeks and on. Furthermore, skin firming up was observed after 4 weeks even when the facial area was treated only once using toxin nano cell 6.

Example 3: Preparation of Hyaluronic Acid in Nano-Encapsulation and Transdermal Delivery In accordance with the aforementioned embodiments of the present disclosure, the exemplary method for preparing biomolecules in nano-encapsulation may be used to prepare a plurality of large molecular weighted biomolecules including hyaluronic acid (HA) with 1500 KDa. Example 3 described the preparation process of HA in nano-encapsulation and its transdermal delivery in therapeutic and cosmeceutical applications.

Preparation of HA Nano Cell 1

Figure 8:
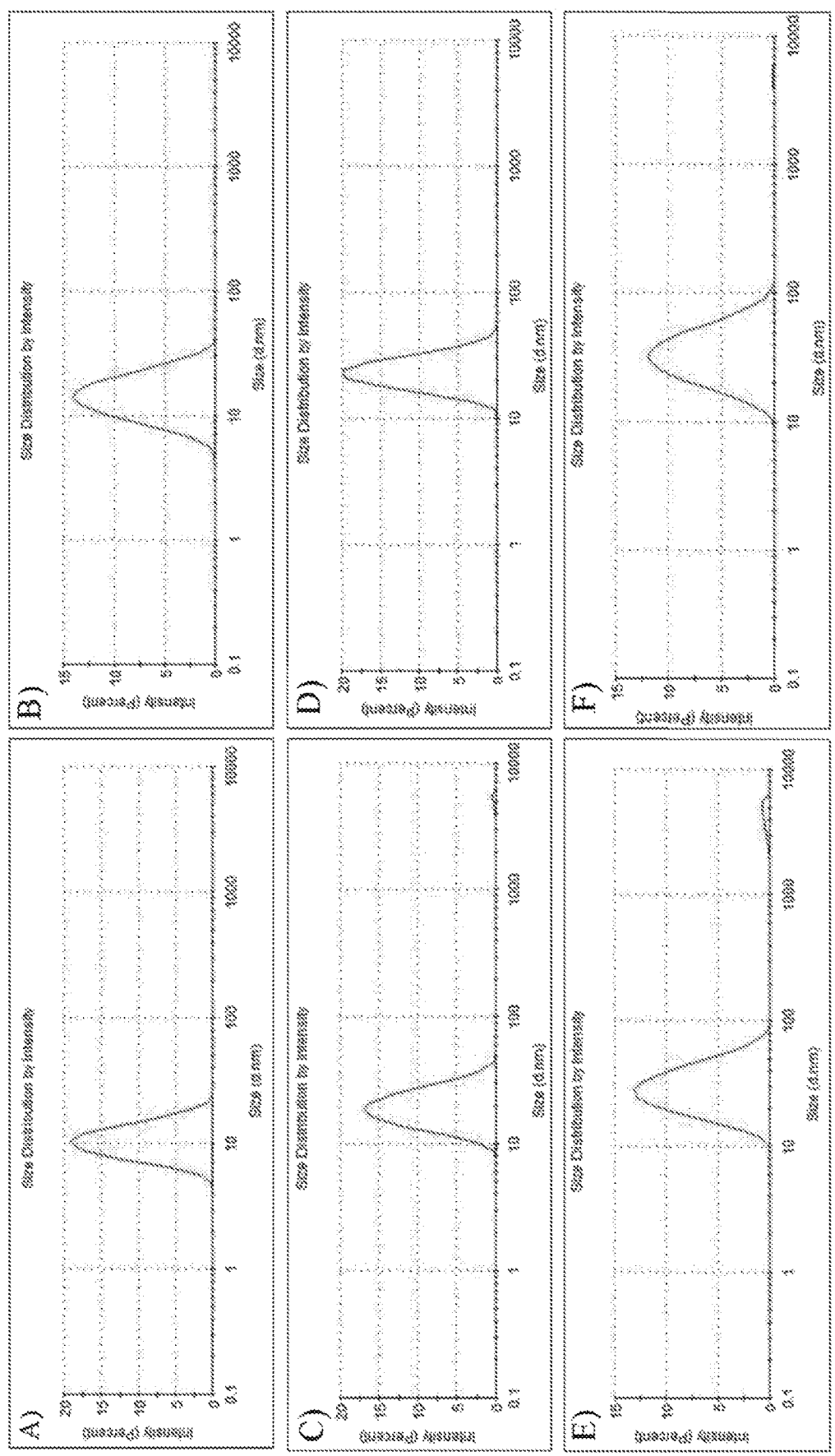
FIG. 8 illustrates particle size and distribution of nano cell encapsulated with large-molecular weighted hyaluronic acid using an exemplary method for preparing biomolecules in nano-encapsulation according to various embodiments of the present disclosure.

In accordance with the aforementioned embodiments accompanied by e.g., FIGS. 5A and 5B, nano cell encapsulated with HA biomolecules were formed, and the size distribution of the HA nano cell during each preparation process was monitored. Particularly, to prepare HA nano cell 1, 180 mg of PEG-40 hydrogenated castor oil liquid (warmed up to approximately 40° C. to melt) was added into a 10 g of aqueous solution containing 0.1% HA (together with 20 ppm Cu-GHK tripeptide, 10 ppm palmitoyl-KTTKS pentapeptide and 10 ppm hexapeptide argireline) in a container at approximately 40° C. and mixed well with stirring. The stirring was kept for approximately 30 minutes until a clear solution was formed. The resulted clear solution including HA nano cell 1 was measured for particle size and zeta potential using the particle size analyzer. As illustrated in FIG. 8A and Table 9, an average particle size of the formed HA nano cell 1 was 9.91 nm by intensity (z average). Further, the particle size was distributed from 7.04 nm (at 10% accumulative volume) to 15.30 nm (at 90% accumulative volume) by volume distribution.

It should be noted that the above preparation of HA nano cell 1 with an oil-in-water structures was for exemplary purposes only. Alternatively, HA may be included in water phase core encapsulated by an oil phase layer according to S502 of FIG. 5B, for which the present disclosure is not intended to limit. When HA was included in the structures of nano cell 1B, that is, in the water phase core of the nano cell, the following repeatable encapsulation steps may also be adjusted accordingly, thereby ensuring each newly formed outer layer having a different polarity from the polarity of the current out layer before the encapsulation process.

Preparation of HA Nano Cell 2

Caprylic/capric triglyceride (10 g) was added into cremophor EL (20 g) and mixed well at approximately 40° C. in a separate container. After that, 0.5 gram of HA nano cell 1 prepared from the above process was added into the mixture, and kept stirred for approximately 30 minutes, until a clear solution was formed. The resulting clear solution containing HA nano cell 2 was measured for particle size and zeta potential. As illustrated in FIG. 8B and Table 9, an average particle size of the formed HA nano cell 2 was 12.90 nm by intensity (z average), and the particle size was distributed from 8.47 nm to 23.70 nm by volume distribution.

Preparation of HA Nano Cell 3

Five grams (5 g) of HA nano cell 2 prepared from the above process was added into 45 g aqueous solution containing 0.1% HA (together with 20 ppm Cu-GHK tripeptide, 10 ppm palmitoyl-KTTKS pentypeptide and 10 ppm hexapeptide argireline, etc.) under stirring at approximately speed of 800 rpm at approximately 40° C. The mixture was kept stirred for approximately 30 minutes until and a bluish transparent solution was obtained. The resulted bluish solution containing HA nano cell 3 were measured for particle size and zeta potential. As illustrated in FIG. 8C and Table 9, an average particle size of HA nano cell 3 was 18.70 nm by intensity (z average), and the particle size was distributed from 12.50 nm to 29.90 nm by volume distribution.

Preparation of HA Nano Cell 4

The preparation of HA nano cell 4 were similar to the above preparation of HA nano cell 2. In particular, caprylic/capric triglyceride (10 g) and cremophor EL (20 g) were mixed well at approximately 40° C., then was added in HA nano cell 3 (0.5 g) prepared from the above process with stirring. The mixture was kept stirred for approximately 15 minutes, until a clear solution containing HA nano cell 4 was obtained. The resulted clear solution was measured for particle size and zeta potential. As illustrated in FIG. 8D and Table 9, an average particle size of HA nano cell 4 was 21.95 nm by intensity (z average) and the particle size was distributed from 16.10 nm to 33.40 nm by volume distribution.

Preparation of HA Nano Cell 5

The preparation of HA nano cell 5 were similar to the above preparation of HA nano cell 3. In particular, 45 g aqueous solution containing 0.1% HA (and 20 ppm Cu-GHK tripeptide, 10 ppm palmitoyl-KTTKS pentypeptide and 10 ppm hexapeptide argireline, etc.) in a container was added in the HA nano cell 4 (5 g) prepared from the above process, at a stirring speed at approximately 800 rpm and a temperature of approximately 40° C. The mixture was kept stirred for approximately 30 minutes until a bluish solution containing HA nano cell 5 was obtained. The resulted bluish solution was measured for particle size and zeta potential. As illustrated in FIG. 8E and Table 9, an average particle size of HA nano cell 5 was 27.65 nm by intensity (z average) and the particle size was distributed from 17.00 nm to 52.80 nm by volume distribution.

Preparation of HA Nano Cell 6

Similar to the preparation process of toxin nano cell 6 containing holo BoNT-A described in Example 2, Cream 1 was firstly prepared according to the components listed in Table 5. Further, the prepared Cream 1 was cooled down to approximately 50° C., one gram of the Cream 1 was added it into the stirring HA nano cell 5 prepared from the above process in a separate container at 40° C. The mixture was kept stirred for approximately 30 minutes, until the HA nano cell 6 (also called as HA nano product) was formed. The formed HA nano cell 6 was then measured for particle size and zeta potential. As illustrated in FIG. 8F and Table 9, an average particle size of HA nano cell 6 was 29.72 nm by intensity (z average) and the particle size was distributed from 18.00 nm to 61.10 nm by volume distribution.

TABLE 9

Particle Size and Distribution of HA Nano Cell

| HA Nano Cell | Average Particle Size (nm) by Intensity | Particle Size (nm) by Volume Distribution (10% Accumulative Volume) | Particle Size (nm) by Volume Distribution (90% Accumulative Volume) |
| --- | --- | --- | --- |
| HA Nano Cell 1 | 9.911 | 7.04 | 15.3 |
| HA Nano Cell 2 | 12.90 | 8.47 | 23.7 |
| HA Nano Cell 3 | 18.70 | 12.5 | 29.9 |
| HA Nano Cell 4 | 21.95 | 16.1 | 33.4 |
| HA Nano Cell 5 | 27.65 | 17.0 | 52.8 |
| HA Nano Cell 6 | 29.72 | 18.0 | 61.1 |

Thermal Stability of HA Nano Cell 6

TABLE 10

Thermal Stability of HA Nano Cell 6 During Freeze Thaw Cycles

| Freeze Thaw Cycle | Temperature (° C.) | HA Nano Cell Particle Size (nm) | Size Change (%) |
| --- | --- | --- | --- |
| Time Zero (initial) | Room Temperature (25° C.) | 29.72 | 0.0 |
| 1st Cycle | −20° C. | 33.52 | 12.8 |
| 2nd Cycle | −20° C. | 32.60 | 9.7 |
| 3rd Cycle | −20° C. | 31.60 | 6.3 |

TABLE 11

Thermal Stability of HA Nano Cell 6

| Storage Temperature | Days of Storage | Particle Size (nm) | Size Change (%) |
| --- | --- | --- | --- |
| Refrigerated Temperature (e.g., 5° C.) | 0 | 29.72 | 0.0 |
| | 7 | 29.39 | −1.1 |
| | 14 | 29.53 | −0.6 |
| | 28 | 30.24 | 1.7 |
| | 60 | 31.00 | 4.3 |
| | 90 | 32.13 | 8.1 |
| | 180 | 32.38 | 9.0 |
| Room Temperature (e.g., 25° C.) | 0 | 29.72 | 0.0 |
| | 7 | 29.06 | −2.2 |
| | 14 | 29.1 | −2.1 |

TABLE 11-continued

Thermal Stability of HA Nano Cell 6

| Storage Temperature | Days of Storage | Particle Size (nm) | Size Change (%) |
| --- | --- | --- | --- |
| | 28 | 30.31 | 2.0 |
| | 60 | 31.07 | 4.5 |
| | 90 | 32.26 | 8.5 |
| | 180 | 32.9 | 10.7 |
| Elevated Temperature (e.g., 40° C.) | 0 | 29.72 | 0.0 |
| | 7 | 29.61 | −0.4 |
| | 14 | 34.57 | 16.3 |
| | 28 | 35.44 | 19.2 |
| | 60 | 37.14 | 25.0 |
| | 90 | 38.73 | 30.3 |
| | 180 | 39.4 | 32.6 |

Similarly, the prepared HA nano cell 6 according to the above processes was further tested for stability for a test period of e.g., 180 days, under different storage conditions, including freeze-thaw cycles, refrigerated conditions (e.g., 2-8° C.), room temperature (e.g., 25° C.) and elevated temperature (e.g., 40° C.), respectively. Table 10 lists an average particle size of HA nano cell 6 and size change during each freeze thaw cycle. Further, Table 11 lists an average particle size of HA nano cell 6 and size change during different thermal conditions. As can be seen, the prepared HA nano cell 6 showed good stability with relatively small size change over a testing period of 6 months, under different thermal conditions during storage, including multiple freeze-thaw cycles, refrigerated storage condition (e.g., 2° C.-8° C.), room temperature (e.g., 25° C.) and elevated temperature (e.g., 40° C.). With the above comparison of different thermal conditions for storage, the HA nano cell 6 were stored at room temperature, which may be sufficient to maintain the bioactivity of HA.

Therapeutic and Cosmeceutical Applications Using HA Nano Cell 6

The prepared HA nano cell 6 were in a form of serum and tested on different skin areas of patients in therapeutic and cosmeceutical applications, for example, wound healing and saggy and rough skin repair.

Figure 9:
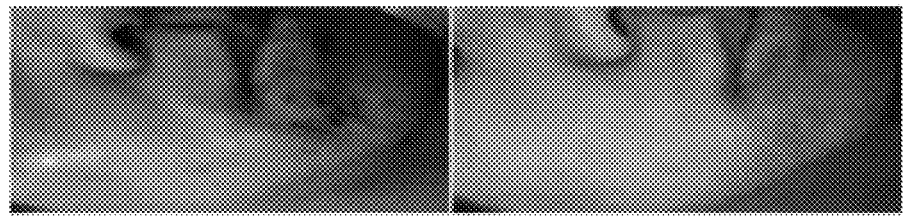
FIG. 9 illustrates comparisons of skin areas of patients applied with nano cell encapsulated with large-molecular weighted hyaluronic acid according to various embodiments of the present disclosure.
Figure 9:
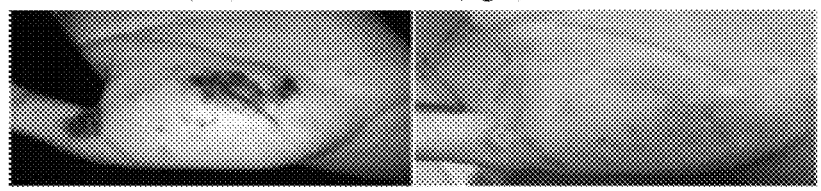
Figure 9:
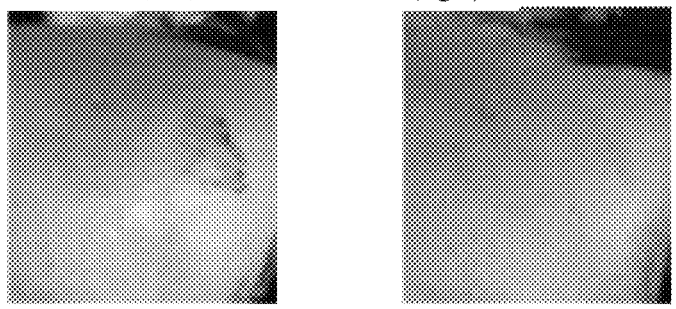
Figure 9:
Figure 9:
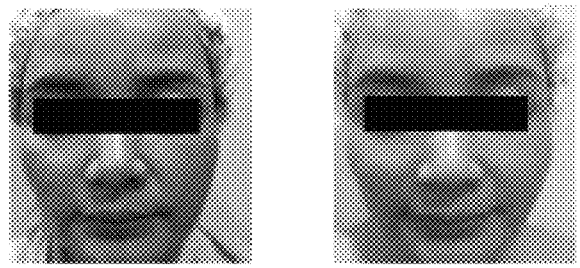

For wound healing, the skin areas of each patient prior to applying the HA nano cell 6 were recorded via color images. After that, approximately 1 mL of serum containing HA nano cell 6 prepared from the above processes was applied on the fresh wounded skin area (which was no longer bleeding) twice per day. The observations were sequentially performed and recorded at the time duration of 1 day, 3 days, and 5 days, respectively. Cases 5-7 of FIG. 9 illustrate comparisons of skin areas of patients applied with the prepared HA in nano-encapsulation for wound healing according to various embodiments of the present disclosure. For newly wounded skin area, after 1 week topical application of the serum containing HA in nano-encapsulation, the wounded area was completely healed with clean skin and no scar.

For saggy and rough skin repair, the treatment of the skin areas with the serum containing HA in nano-encapsulation was similar to those in the application of wound repair. The observations were sequentially performed and recorded at the time duration of 1 week, 2 weeks, and 3 weeks, respectively. Cases 8-9 of FIG. 9 illustrate comparisons of skin areas of patients applied with the prepared HA in nano-encapsulation for saggy and rough skin repair according to various embodiments of the present disclosure. As can be seen, the skin firming-up and visible skin color/tone lightening with reduction of wrinkles was observed after 3 weeks of treatment.

According to the aforementioned embodiments and examples of the present disclosure, the disclosed method for preparing biomolecules in nano-encapsulation (e.g., BoNT-A toxin nano cell and HA nano cell) may produce stable and bioactive nanoparticles which showed clinical improvements as shown in a variety of applications. Such improvement was resulted from the fast and effective delivery of active ingredients (e.g., BoNT-A or HA) encapsulated with the core, or between the multi-layer of the nanoparticles, alternatively, immobilized on the surface of the nanoparticles.

The disclosed method for preparing biomolecules in nano-encapsulation may combine micelles formation process and multiple encapsulation processes as a systematic procedure. Each of the hydrophilic active ingredients may be dissolved a hydrophilic phase for encapsulation process, while each of the hydrophobic active ingredients may be dissolved a hydrophobic phase for encapsulation process. As such, various active ingredients with different polarity and solubility may be encapsulated within a single multi-layer nanoparticle for cross-skin delivery mission, resulting in a multi-layer nanoparticle carrying different active ingredients for realizing multiple functions, which may have significantly more extensive applications compared with nanoparticle only containing a single type of ingredients.

Although the principles and implementations of the present disclosure are described by using specific embodiments in the specification, the foregoing descriptions of the embodiments are only intended to help understand the method and core idea of the method of the present disclosure. Meanwhile, a person of ordinary skill in the art may make modifications to the specific implementations and application range according to the idea of the present disclosure. In conclusion, the content of the specification should not be construed as a limitation to the present disclosure.

What is claimed is:

1. A multilayer nano-cell, comprising:
an innermost water phase core including biomolecules in an aqueous solution, the biomolecules including hyaluronic acid, and the aqueous solution including Cu-GHK tripeptide, palmitoyl-KTTKS pentapeptide, and hexapeptide argireline;
a first layer, including an oil phase layer encapsulating the innermost water phase core, thereby forming a water-in-oil structure, wherein the oil phase layer includes caprylic/capric triglyceride and macrogol-35-glycerol-rizinoleat;
a second layer, including a water phase layer encapsulating the first layer, the water phase layer including hyaluronic acid, Cu-GHK tripeptide, palmitoyl-KTTKS pentapeptide, and hexapeptide argireline;
a third layer, including another oil phase layer encapsulating the second layer;
a fourth layer, including another water phase layer encapsulating the third layer;
a fifth layer, including another oil phase layer encapsulating the fourth layer; and
a sixth layer, including an outmost cream layer encapsulating the fifth layer.

2. The multilayer nano-cell according to claim 1, wherein:
the multilayer nano-cell has an average size ranging from about 10 nanometers to about 100 nanometers.

3. The multilayer nano-cell according to claim 1, wherein:
an average size of the water-in-oil structure is in a range of 3 nanometers to 20 nanometers.

4. The multilayer nano-cell according to claim 1, wherein:
the outmost cream layer includes a water phase mixture and an oil phase mixture,
the water phase mixture includes at least one of glycerin, dipotassium glycyrrhizate, petylene glycol, propylene glycol, methylparaben and carbomer, and
the oil phase mixture includes at least one of mineral oil, cetearyl alcohol, propylparaben, methylparaben, polyethylene glycol (PEG)-100 stearate, PEG-40 hydrogenated castor oil, caprylic/capric triglyceride, polysorbate-80, macrogol-35-glycerol-rizinoleat, glyceryl stearate, polysorbate-65, polysorbate-60, polysorbate-20, soybean oil, tea oil, vegetable oil, sunflower seed oil, fish oil, sesame oil, vitamin E, animal lipid oil, octanoic acid decanoic acid ester of glycerol, lecithin egg phosphatidylcholine (EPC), poly(propyleneoxide) (PPO), poly(D, L-lactic acid) (PDLLA), poly(ε-caprolactone) (PCL), poly(L-aspartate) and poloxamers, PEG-polyglutamate, PEG-polyaspartate, PEG-poly-L-lactide, sorbitane monopalmitate, and sorbitan oleate.

5. The multilayer nano-cell according to claim 1, wherein:
the another water phase layer includes hyaluronic acid, Cu-GHK tripeptide, palmitoyl-KTTKS pentapeptide, and hexapeptide argireline; and
each of the another oil phase layers includes caprylic/capric triglyceride and macrogol-35-glycerol-rizinoleat.

6. The multilayer nano-cell according to claim 1, wherein:
each of the another oil phase layers further includes one or more of hydrogenated castor oil, Caprylic/capric triglyceride, polysorbate, soybean oil, sorbitan oleate, vitamin E, mineral oil, cetearyl alcohol, propylparaben, methylparaben, polyethylene glycol (PEG-100) stearate.

7. The multilayer nano-cell according to claim 1, wherein:
the water phase layer in the second layer further includes one or more of, cell growth factors, stem cells, stem cell liquids, peptides, proteins, aptamers, oligo-nucleotides, vitamins, Snap-8 octapeptide, di-peptides, allantoin, niacinamide, aloe vera, Co-enzymes, resveratrol, palmitoyl-KTTKS, palmitoyl-GHK, palmitoyl-GQPR, palmitoyl-oligopeptides, aptamers, si-RNAs, stem cells, botulinum neurotoxin, and therapeutic agents.

8. The multilayer nano-cell according to claim 7, wherein:
the therapeutic agents include one or more selected from insulin, celecoxib, rofecoxib, 5-floro-uracil, diacarbazine, ibuprofen, tetracycline, oxytetracycline, estriol, progesterone, doxycycline, minocycline, estradiol, silver ions including $AgNO_3$, Zn ions including ZnO, and plant extracts.

9. The multilayer nano-cell-according to claim 1, wherein:
the first layer of the multilayer nano-cell provides a particle size distributed from 7.04 nm to 15.3 nm by a volume distribution;
the second layer of the multilayer nano-cell provides a particle size distributed from 8.47 nm to 23.7 nm by a volume distribution;
the third layer of the multilayer nano-cell provides a particle size distributed from 12.5 nm to 29.9 nm by a volume distribution;

the fourth layer of the multilayer nano-cell provides a particle size distributed from 16.1 nm to 33.4 nm by a volume distribution;

the fifth layer of the multilayer nano-cell provides a particle size distributed from 17.0 nm to 52.8 nm by a volume distribution; and the six layer of the multilayer nano-cell provides a particle size distributed from 18.0 nm to 61.1 nm by a volume distribution.

\* \* \* \* \*